(12) United States Patent
Altschuler et al.

(10) Patent No.: US 8,790,681 B2
(45) Date of Patent: Jul. 29, 2014

(54) SOLID FORMS FOR TISSUE REPAIR

(75) Inventors: Nir Altschuler, Hod Hasharon (IL); Razi Vago, Lehavim (IL)

(73) Assignee: Cartiheal (2009) Ltd., Ariel (IL)

( * ) Notice: Subject to any disclaimer, the term of this patent is extended or adjusted under 35 U.S.C. 154(b) by 0 days.

(21) Appl. No.: 13/378,474

(22) PCT Filed: May 23, 2010

(86) PCT No.: PCT/IL2010/000410
§ 371 (c)(1),
(2), (4) Date: Mar. 5, 2012

(87) PCT Pub. No.: WO2010/146575
PCT Pub. Date: Dec. 23, 2010

(65) Prior Publication Data
US 2012/0177702 A1  Jul. 12, 2012

Related U.S. Application Data

(60) Provisional application No. 61/187,081, filed on Jun. 15, 2009, provisional application No. 61/252,800, filed on Oct. 19, 2009.

(51) Int. Cl.
| | |
|---|---|
| *A61F 13/00* | (2006.01) |
| *A61F 2/00* | (2006.01) |
| *A61F 2/28* | (2006.01) |
| *A61F 2/02* | (2006.01) |
| *A61L 27/38* | (2006.01) |
| *A61L 27/56* | (2006.01) |
| *A61L 27/36* | (2006.01) |
| *A61L 27/34* | (2006.01) |
| *A61L 27/42* | (2006.01) |
| *A61F 2/30* | (2006.01) |

(52) U.S. Cl.
CPC ..... *A61F 2/30756* (2013.01); *A61F 2002/3092* (2013.01); *A61F 2/3094* (2013.01); *A61F 2/28* (2013.01); *A61F 2002/30011* (2013.01); *A61L 27/3834* (2013.01); *A61L 27/56* (2013.01); *A61F 2230/0069* (2013.01); *A61L 27/3604* (2013.01); *A61L 2430/02* (2013.01); *A61F 2310/00341* (2013.01); *A61L 27/34* (2013.01); *A61F 2002/30807* (2013.01); *A61L 27/427* (2013.01); *A61L 2430/06* (2013.01); *A61F 2002/30224* (2013.01); *A61F 2250/0023* (2013.01)
USPC ..... 424/423; 424/426; 623/16.11; 623/23.58; 623/23.72; 623/23.75; 623/23.76

(58) Field of Classification Search
None
See application file for complete search history.

(56) References Cited

U.S. PATENT DOCUMENTS

| | | | |
|---|---|---|---|
| 6,322,592 B2 | 11/2001 | Lucas et al. | |
| 6,995,013 B2 * | 2/2006 | Connelly et al. | 435/395 |

(Continued)

FOREIGN PATENT DOCUMENTS

| | | |
|---|---|---|
| CA | 2633808 A1 | 7/2007 |
| CA | 2635023 A1 | 7/2007 |

(Continued)

OTHER PUBLICATIONS

International Search Report (ISR) for PCT/IL2010/000410; I.A. fd: May 23, 2010, mailed Nov. 17, 2010, from the United States Patent and Trademark Office, Alexandria, VA.

(Continued)

*Primary Examiner* — Carlos Azpuru
*Assistant Examiner* — Casey Hagopian
(74) *Attorney, Agent, or Firm* — Sterne, Kessler, Goldstein & Fox P.L.L.C.

(57) ABSTRACT

This invention provides aragonite- and calcite-based scaffolds for the repair, regeneration, enhancement of formation or a combination thereof of cartilage and/or bone, which scaffolds comprise at least two phases, wherein each phase differs in terms of its chemical content, or structure, kits comprising the same, processes for producing solid aragonite or calcite scaffolds and methods of use thereof.

20 Claims, 11 Drawing Sheets

(56) References Cited

U.S. PATENT DOCUMENTS

| | | | |
|---|---|---|---|
| 7,375,077 B2 | 5/2008 | Mao | |
| 7,709,442 B2 | 5/2010 | Mao | |
| 2003/0003127 A1 | 1/2003 | Brown et al. | |
| 2003/0114936 A1* | 6/2003 | Sherwood et al. | 623/23.58 |
| 2003/0236573 A1 | 12/2003 | Evans et al. | |
| 2005/0074877 A1 | 4/2005 | Mao | |
| 2005/0177118 A1 | 8/2005 | Hoganson et al. | |
| 2008/0065210 A1 | 3/2008 | McKay | |
| 2008/0249632 A1 | 10/2008 | Stone et al. | |
| 2008/0274185 A1 | 11/2008 | Mao | |
| 2008/0281431 A1 | 11/2008 | Missos | |
| 2011/0200563 A1 | 8/2011 | Vago | |
| 2011/0256228 A1 | 10/2011 | Altschuler et al. | |
| 2012/0189669 A1 | 7/2012 | Altschuler et al. | |

FOREIGN PATENT DOCUMENTS

| | | |
|---|---|---|
| CA | 2635233 A1 | 7/2007 |
| EP | 1 270 025 A1 | 1/2003 |
| EP | 1 604 696 A1 | 12/2005 |
| WO | WO 99/02200 A1 | 1/1999 |
| WO | WO 2010/146574 A1 | 12/2010 |

OTHER PUBLICATIONS

International Preliminary Report on Patentability (Chapter I of the Patent Cooperation Treaty) including the Written Opinion of the International Searching Authority for PCT/IL2010/000410; I.A. fd: May 23, 2010, issued Dec. 16, 2011, from the International Bureau of WIPO, Genera, Switzerland.
Vago, R, "Beyond the skeleton: Cnidarian biomaterials as bioactive extracellular microenvironments for tissue engineering," Organogenesis 4(1): 18-22 (Jan. 2008), Landes Bioscience, Austin, Texas.
Wu, YC et al., "A comparative study of the physical and mechanical properties of three natural corals based on the criteria for bone-tissue engineering scaffolds," J Mater Sci Mater Med 20(6): 1273-1280 (Jun. 2009), Springer, Norwell, MA.
Kreklau, B et al., "Tissue engineering of biphasic joint cartilage transplants," Biomaterials, Sep. 1999; 20(18): 1743-1749, Elsevier Science, Amsterdam, Netherlands.
Gravel, M et al., "Responses of mesenchymal stem cell to chitosan-coralline composites microstructured using coralline as gas forming agent," Biomaterials, Mar. 2006; 27(9): 1899-1906, Elsevier Science, Amsterdam, Netherlands.
Spassova, E. et al, "Chemistry, ultrastructure and porosity of monophasic and biphasic bone forming materials derived from marine algae," Mat.-wiss. u. Werkstofftech., Dec. 2007, 38:1027-1034, VCH Verlagsgesellschaft, Weinheim, Germany.
Gravel, M et al., "Use of Natural Coralline Biomaterials As Reinforcing and Gas-Forming Agent for Developing Novel Hybrid Biomatrices: Microarchitectural and Mechanical Studies," Tissue Engineering, Mar. 2006, 12(3): 589-600, Mary Ann Liebert, Inc., New York, New York.
Vecchio, KS et al., "Conversion of sea urchin spines to Mg-substituted tricalcium phosphate for bone implants," Acta Biomater, Sep. 2007; 3(5): 785-793, Elsivier, Oxford, UK.

Ripamonti, U, "The morphogenesis of bone in replicas of porous hydroxyapatite obtained from conversion of calcium carbonate exoskeletons of coral," J Bone Joint Surg Am, Jun. 1991; 73(5): 692-703, Journal of Bone and Joint Surgery publisher, Boston, MA.
Kühne, JH et al, "Bone formation in coralline hydroxyapatite. Effects of pore size studied in rabbits," Acta Orthop Scand, Jun. 1994; 65(3): 246-252, Taylor & Francis, Basingstoke, Hampshire, UK.
Ben-Nissan, B et al., "Morphology of sol-gel derived nano-coated coralline hydroxyapatite," Biomaterials, Sep. 2004; 25(20): 4971-4975, Elsevier Science, Amsterdam, Netherlands.
Mansur, HS et al.,"XRD, SEM/EDX and FTIR Characterization of Brazilian Natural Coral," Key Engineering Materials, 2005, vol. 284-286, pp. 43-46, Volume name: Bioceramics 17, Proceedings of the 17th International Symposium on Ceramics in Medicine, The Annual Meeting of the International Society for Ceramics in Medicine, New Orleans, Louisiana, USA, Dec. 8-12, 2004, Editors: Panjian Li, et al, eds, Trans Tech Publications Ltd, Aedermannsdorf, Switzerland.
Excerpted file history of U.S. Appl. No. 13/130,272, Altschuler et al.: "Interview Summary" filed Mar. 25, 2014 and "Notice of Allowance and fees Due" dated Apr. 11, 2014.
Excerpted file history of U.S. Appl. No. 13/378,458, Altschuler et al., (Jan. 17, 2014-Mar. 18, 2014).
Excerpted file history of U.S. Appl. No. 13/130,272, Altschuler et al., (Jan. 6, 2014-Feb. 28, 2014).
Excerpted file history of U.S. Appl. No. 13/378,458, Altschuler et al., (through Dec. 9, 2013).
Excerpted file history of U.S. Appl. No. 13/130,272, Altschuler et al., (through Sep. 4, 2013).
Excerpted file history of U.S. Appl. No. 12/743,812, Vago, (through Sep. 18, 2013).
Peretz, H et al., "Superior survival and durability of neurons and astrocytes on 3-dimensional aragonite biomatrices," Tissue Eng, Mar. 2007; 13(3): 461-472, Mary Ann Liebert, Inc., New Rochelle, NY.
Petite, H et al., "Tissue-engineered bone regeneration," Nat Biotechnol, Sep. 2000; 18(9): 959-963, Nature Pub. Co., New York, NY.
Abstract of: Tang, YC, et al., ["A study on repairing mandibular defect by means of tissue-engineering and human bone morphogenetic protein-2 gene transfection in osteoporotic rats"], Zhonghua Kou Qiang Yi Xue Za Zhi (Chinese Journal of Stomatology), Jul. 2006;41(7): 430-431, Chinese Medical Association, Beijing, China.
Guillemin, G et al., "Comparison of coral resorption and bone apposition with two natural corals of different porosities," J Biomed Mater Res, Jul. 1989; 23(7): 765-779, Wiley, Hoboken, N.J.
Abramovitch-Gottlib, L et al., "Biofabricated marine hydrozoan: a bioactive crystalline material promoting ossification of mesenchymal stem cells," Tissue Eng, Apr. 2006; 12(4): 729-739, Mary Ann Liebert, Inc., New Rochelle, NY.
Vuola, J., "Natural coral and hydroxyapatite as bone substitutes," Academic Dissertation, Jan. 5, 2001, Department of Plastic Surgery, Helsinki University Central Hospital, Helsinki, Finland.
Kim, IL et al., "Hydrogel design for cartilage tissue engineering: a case study with hyaluronic acid," Biomaterials, Dec. 2011; 32(34): 8771-8782, Elsevier Science, Amsterdam, Netherlands.
O'Reilly, S, "Progress in Cartilage Repair: The Holy Grail of Knee OA," Medtech Insight (newsletter), Oct. 2013, pp. 1-10, Windhover Information, Elsevier Business Intelligence, Philadelphia, PA.

\* cited by examiner

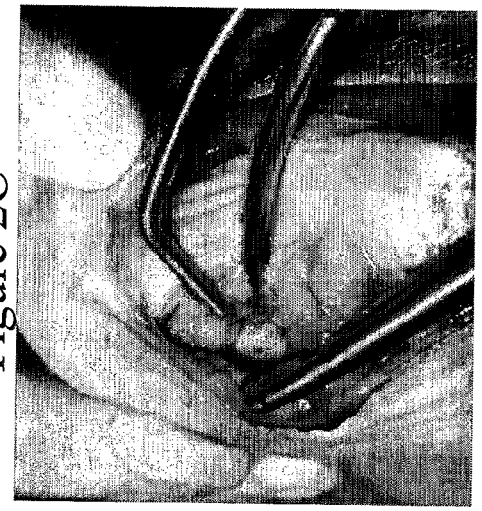

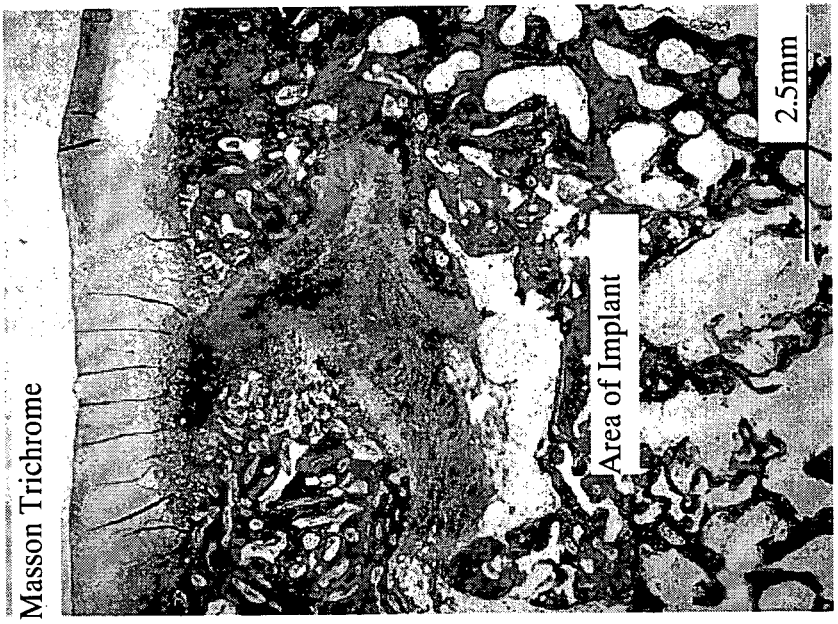
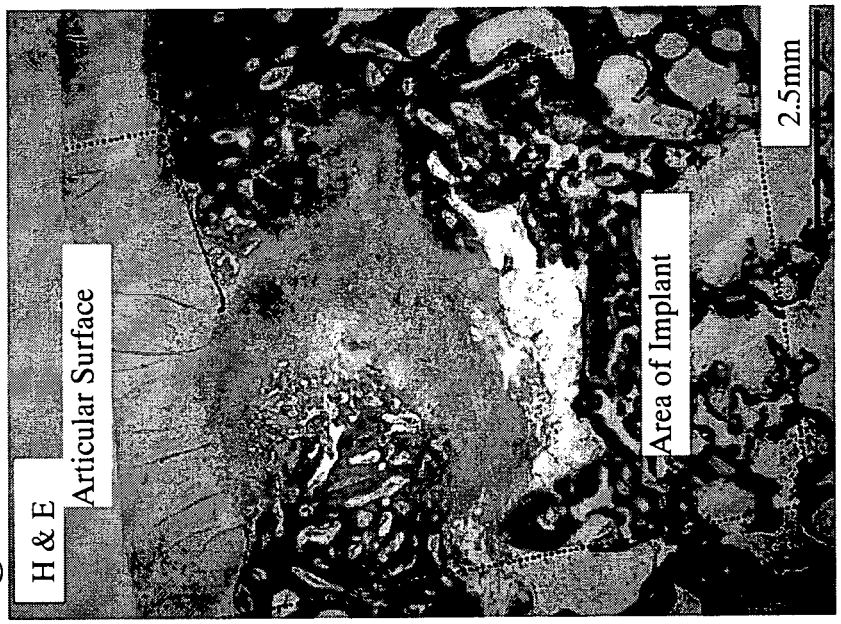

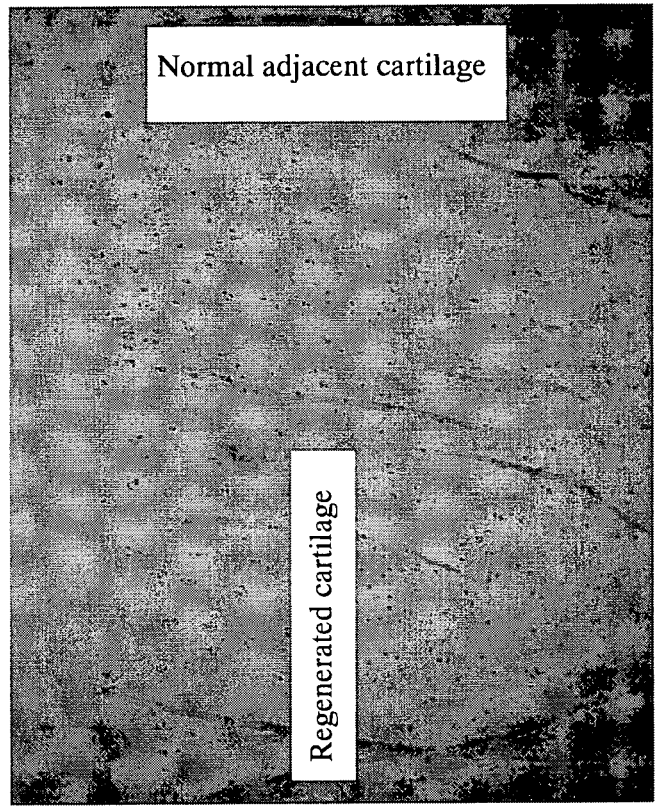
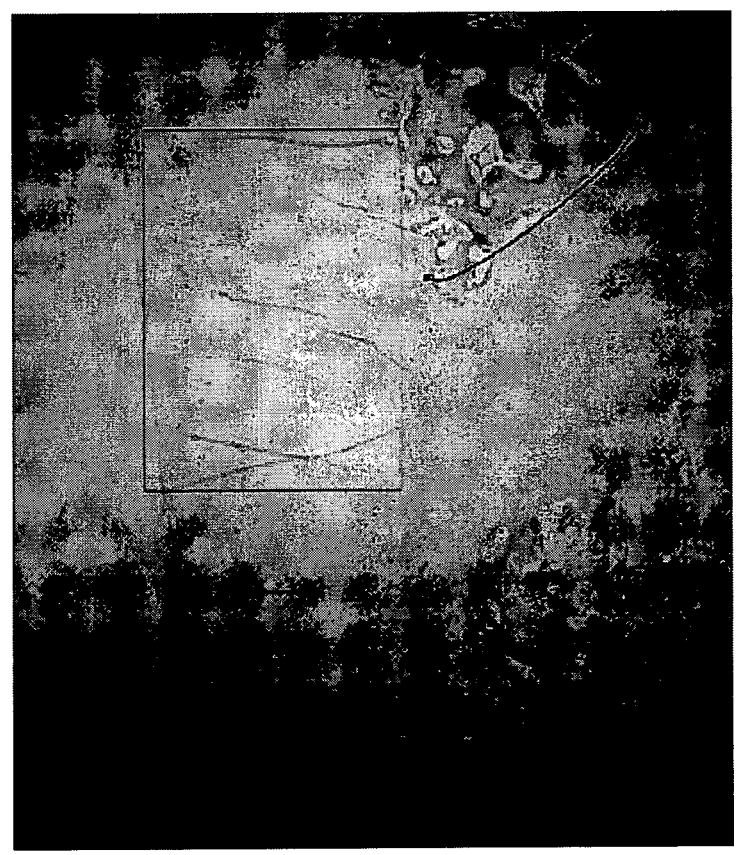
Figure 5B
Figure 5A 0.5 mm   Top phase: ~85-90% porosity
0.5 mm   Intermediate phase1: ~70-80% porosity
0.5 mm   Intermediate phase 2: ~60-70% porosity 6 mm     Bottom phase: ~45-55% porosity

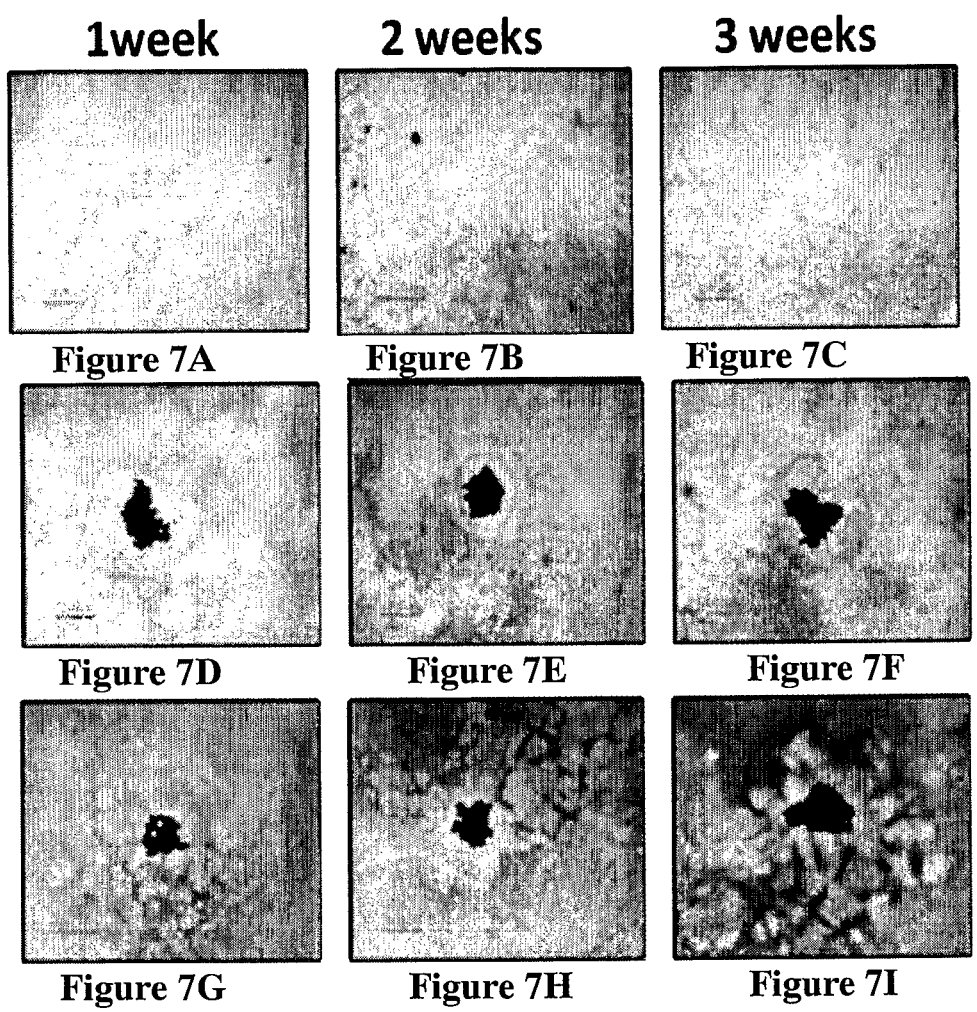

SEM: MSCs on Coral

SEM: MSCs on Coral + Hyaluronic Acid

SOLID FORMS FOR TISSUE REPAIR

BACKGROUND OF THE INVENTION

Surgical intervention and grafting are sometimes necessary to restore mechanical function and reconstruct the morphology of bone and cartilage, resulting from trauma, tumors, or abnormal bone developments.

Synthetic materials such as metals and bone cements have also been used for restoring and reconstructing bone for many years, but often result in stress-shielding to the surrounding bone and fatigue failure of the implant. Another possibility is autologous bone grafting, although the supply of autologous bone tissue is limited and its collection is painful, with the risk of infection, hemorrhage, cosmetic disability, nerve damage, and loss of bone function. In addition, significant morbidity is associated with autograft harvest sites. These problems may be overcome by engineering tissue using scaffolds made of synthetic or natural biomaterials that promote the adhesion, migration, proliferation, and differentiation of bone marrow stem cells, also known as mesenchymal stem cells (MSCs). An association between biocomponents and biologic regenerative and repair responses can be promoted by providing a scaffold containing spaces morphologically compatible with osteons and their vascular interconnections.

The immediate microenvironment and the three-dimensional (3D) organization are important factors in differentiation in general and particularly in chondrogenic and osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans).

Osteoarthritis (OA) results from general wear and tear of joints, most notably hip and knee joints. Osteoarthritis is common in the elderly but, in fact, by age 40 most individuals have some osteoarthitic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not posses the capacity for self-repair. Attempts to re-grow hyaline cartilage for repair of cartilage defects remain unsuccessful. Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

An ideal material which restores mechanical function and reconstructs the morphology of bone and cartilage is as yet, lacking.

SUMMARY OF THE INVENTION

In some embodiments, the present invention provides coralline-based scaffolds for inducing or enhancing repair, regeneration or enhancement of formation of cartilage or bone, or a combination thereof, wherein said scaffold comprises aragonite or calcite.

In some embodiments, the invention provides a scaffold for tissue repair, said scaffold consisting essentially of two phases wherein:
  a first phase of said two phases comprises solid coral or biolattice comprising a biocompatible polymer and said first phase further comprises a series of hollows along a longitudinal axis in said first phase, wherein said biocompatible polymer is substantially located within said series of hollows; and
  a second phase of said two phases comprises a solid coral or biolattice.

In one embodiment, the present invention provides a scaffold for repair, regeneration or enhancement of formation of cartilage or bone, or a combination thereof, which scaffold consists of a solid form of aragonite or calcite and further comprises:
  at least a first phase, comprising voids having an average diameter ranging from about 60-160 µm; and
  at least a second phase, comprising voids having an average diameter ranging from about 170-850 µm.

In some embodiments, according to this aspect, the scaffold further comprises a third phase, comprising voids having an average diameter ranging from about 170-300 µm and said second phase comprises voids having an average diameter ranging from about 350-850 µm and said third phase is positioned between said first and second phase.

In another embodiment, the invention provides a scaffold for repair, regeneration or enhancement of formation of cartilage or bone, or a combination thereof, which scaffold consists of a solid form of aragonite or calcite and further comprises:
  at least a first phase, comprising pores having a pore volume (porosity) ranging from about 35-55%; and
  at least a second phase, comprising pores having a pore volume (porosity) ranging from about 56-95%.

In some embodiments, according to this aspect, the scaffold further comprises a third phase, comprising pores having a pore volume ranging from about 56-80%, wherein said second phase comprises voids having pore volume (porosity) ranging from about 81-95% and said third phase is positioned between said first and second phase.

In another embodiment, this invention provides a scaffold for the repair, regeneration or enhancement of formation of cartilage, bone, or a combination thereof, which scaffold consists of a solid form of aragonite or calcite isolated from a coral and further comprises:
  at least a first phase, comprising voids having an average diameter, pore volume or combination thereof, which corresponds to that of the native coral from which said solid form was isolated; and at least a second phase, comprising voids having an average diameter, pore volume or combination thereof, which average void diameter, pore volume or combination thereof is greater than that of said first phase by from about 15-100%.

In some embodiments, according to this aspect, the scaffold further comprises a third phase, comprising voids having an average diameter, pore volume or combination thereof, which average pore diameter, pore volume or combination thereof is greater than that of said first phase by from about 15-35% and said second phase comprises voids having an average diameter, pore volume or combination thereof, which average pore diameter, pore volume or combination thereof is greater than that of said first phase by from about 40-100% and said third phase is positioned between said first and second phase.

In another embodiment, this invention provides a process for the preparation of a multi-phasic scaffold for inducing or enhancing cartilage or bone formation or repair, or a combination thereof, said process comprising the steps of:

contacting only a portion of a solid form of aragonite or calcite with a calcium chelator and an acid to yield a solid form comprising enlarged voids in at least a portion of said solid form; and washing and drying said solid form under applied negative pressure.

According to this aspect, and in some embodiments, the contacting is conducted over a duration and under conditions, which vary as a consequence of the desired final geometry of the scaffold.

According to this aspect, and in other embodiments, the solid form produced by said process comprises at least two phases, which phases differ in their pore volume (porosity), or which phases comprise voids which differ in terms of the average diameter of said voids, or a combination thereof.

In some embodiments, this invention provides a scaffold produced according to a process of this invention.

In one embodiment, this invention provides a scaffold for repair of cartilage comprising a biolattice consisting essentially of calcite capable of being inserted within a site of cartilage repair. In some embodiments, the biolattice is derived from *Tetraclita rufotincta*.

In one embodiment, this invention provides a method of inducing or enhancing cartilage or bone formation or repair, or a combination thereof, said method comprising implanting in a subject, any scaffold of this invention within a site in need of cartilage or bone formation, repair or a combination thereof.

According to this aspect, and in some embodiments, the method comprises exposing said site in need of cartilage or bone formation or repair or a combination thereof, and optionally exposing bone tissue located proximally to the site of cartilage repair in said subject in need of cartilage repair or regeneration, prior to implanting said scaffold.

According to this aspect, and in some embodiments, the method for inducing or enhancing cartilage repair or regeneration comprises the step of affixing at least a portion of said scaffold within bone located proximally to said site of cartilage repair In another embodiment, this invention provides a process for the purification of coralline-based scaffolding, said process comprising the steps of:

contacting solid aragonite of a desired size and shape with a solution comprising an oxidizing agent; and
washing and drying said solid aragonite whereby one or each of said steps is conducted under applied negative pressure.

According to this aspect, and in some embodiments, the process comprises conducting said contacting under mildly acidic conditions. In some embodiments, the solution comprises sodium hypochlorite.

According to this aspect, and in some embodiments, the process further comprises subjecting the solid aragonite to a temperature of at least 275° C under applied negative pressure.

In some embodiments, the applied negative pressure ranges between about 0.2 to 0.00001 Bar, or in some embodiments, the applied negative pressure ranges between 0.4 to 0.0000001 Bar.

In some embodiments, the invention provides a coralline-based scaffolding produced by the process according to this aspect of the invention.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 2 depicts successful incorporation of embodiments of a scaffold of this invention within a cartilage and bone defect. FIG. 2A shows a photograph of a drilled hole in a medial femoral condyle of a goat; D=6 mm, L=7.5 mm. FIGS. 2B and 2C show a photograph of implantation of the scaffold within the site of injury. FIG. 2D shows that at 19 days post implantation: the implant was successfully incorporated within the cartilage, signs of vascularization and an intact meniscus are seen.

FIG. 3 shows light micrographs of osteochondral tissue in which an embodied scaffold of this invention has been implanted. FIG. 3A shows a low magnification (2×) 9 weeks after implantation of an embodied scaffold described herein in a medial femoral condyle of a goat; D=5.2 mm, L=7.5 mm; visualized with standard H & E staining. FIG. 3B shows a comparable section of the tissue stained with Masson Trichrome. Note that the area of implant, (highlighted by the dotted rectangle in 3A) is replaced by woven bone, cartilage and fibrous tissue.

FIG. 4, similar to FIG. 3 shows light micrographs of osteochondral tissue in which an embodied scaffold of this invention has been implanted, subjected to different staining protocols. FIG. 4A demonstrates the presence of a homogeneous red band of cartilage covering normal bone and the area of defect. Similarly, FIG. 4B shows positive staining for collagen type II along the band of cartilage covering the defect (and adjacent normal cartilage as an internal positive control).

FIG. 5 shows light micrographs of osteochondral tissue in which an embodied scaffold of this invention has been implanted, subjected to H & E staining. The section is from a medial femoral condyle of a goat, harvested 9 weeks after implantation of the scaffold; D=5.2 mm, L=7.5 mm. FIG. 5A is a low magnification of the tissue, while FIG. 5B is a higher magnification of the insert seen in FIG. 5A. Note the uniformity of the tissue in the region of the hyaline cartilage (inset). There is slight clustering of chondrocytes within the region of regeneration, but the region otherwise appears comparable to neighboring cartilage tissue.

FIG. 7 shows micrographs of Safranin O/Fast Green staining of MSC cultures, indicating the chondrogenic potential of the implant as a function of whether the cells were cultured on Aragonite (FIGS. 7D, 7E and 7F), Aragonite and Hyaluronic Acid (FIGS. 7G, 7H and 7I) or without any scaffold (control) (FIGS. 7A, 7B and 7C) over time.

FIG. 11C shows an embodied scaffold, stained with fast green, which selectively stains the hyaluronic acid component of the scaffold.

DETAILED DESCRIPTION OF THE PRESENT INVENTION

Figure 1:
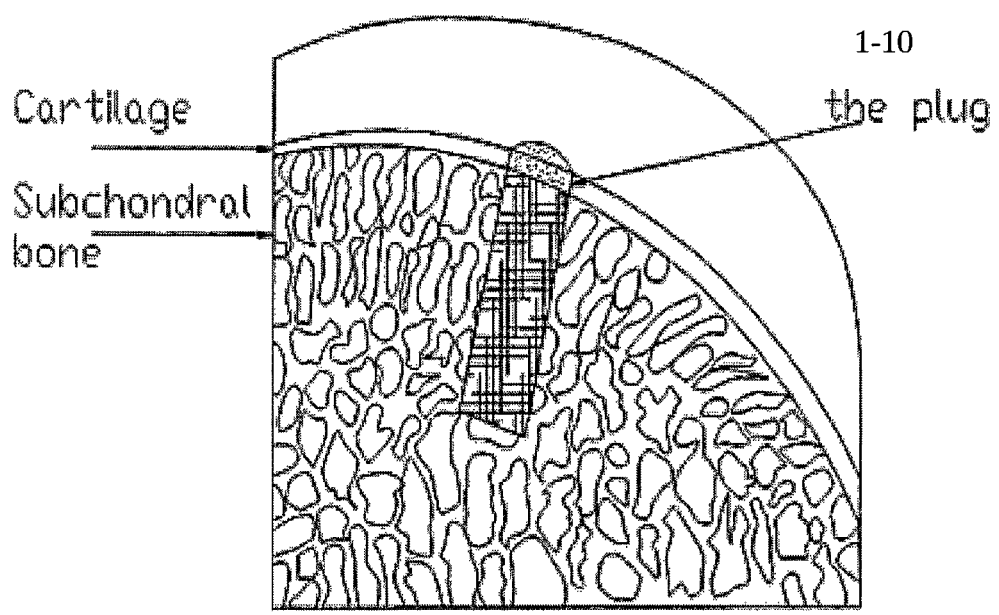
FIG. 1 schematically depicts positioning an implant within a site for cartilage and bone repair, wherein the scaffold 1-10 is positioned such that a first phase is positioned within the cartilage and a second phase is positioned within proximally located bone.

This invention provides, inter alia, scaffolds, tools and methods of use thereof for repair and/or formation of cartilage and/or bone tissue in a subject. This invention further provides kits for repair and/or formation of cartilage and/or bone tissue in a subject.

Coral, which is comprised of $CaCO_3$ in the crystalline form of aragonite or calcite has the advantage of supporting fast cellular invasion, adherence, proliferation and differentiation of mesenchymal stem cells into cartilage and/or bone tissue.

Three-dimensional (3-D) coral scaffolds attract mesenchymal stem cells from surrounding or proximally located tissue and promote blood vessel formation to a site of cartilage repair. Such scaffolds can be used for regeneration, repair and enhancement of formation of cartilage and/or bone in a subject for the treatment of full-thickness cartilage defects, partial thickness cartilage defects and/or osteochondral defects.

The terms "coral" and "aragonite" are used interchangeably herein

The coralline-based or calcite-based scaffolds of this invention may also be used for regeneration, repair and enhancement of formation of bone in a subject, for the treatment of a bone condition, disease or disorder.

This invention provides the unexpected application of coral or calcite scaffolding alone being useful in cartilage and/or bone regeneration, repair and enhancement of formation and moreover, that coral/calcite scaffolding can be prepared and inserted specifically and optimally within cartilage and/or bone in a subject in need thereof, for methods of cartilage and/or bone regeneration, repair and enhancement of formation.

In particular, this invention provides the unexpected application that cartilage and/or bone regeneration, repair and enhancement of formation is optimal when the coral scaffolding consists essentially of two phases wherein a first phase of said two phases comprises solid coral or biolattice comprising a biocompatible polymer and the first phase further comprises a series of hollows along a longitudinal axis in the first phase, wherein the biocompatible polymer is substantially located within said series of hollows; and a second phase of said two phases comprises a solid coral or biolattice alone.

In particular, this invention provides the unexpected advantage in terms of greater chondrogenesis, when the scaffolds as herein described incorporate a biocompatible polymer such as hyaluronic acid in the phase inserted within cartilage. Another advantage to the scaffolds according to this aspect, is the presence of pre-drilled channels or longitudinally placed holes within the phase containing the biocompatible polymer such as hyaluronic acid, which holes are impregnated with the biocompatible polymer such as hylauronic acid and serve as a reservoirs for the biocompatible polymer such as hyaluronic acid in a phase located within a region in need of cartilage repair. Localization of the biocompatible polymer such as hyaluronic acid allows for greater direction of migrating progenitor cells throughout the phase of this scaffold to stimulate cartilage regeneration and repair. In some embodiments, the channels comprising concentrated biocompatible polymer such as hyaluronic acid within the voids along the longitudinal axis of the phase of the scaffold provide a chemotactic guide for recruited cells involved in chondrogenesis, and/or in some embodiments, influence local recruitment and differentiation of the chondrogenic population of cells migrating thereto. In some embodiments, the channels comprising concentrated biocompatible polymer such as hyaluronic acid within the voids along the longitudinal axis of the phase of the scaffold contribute to cartilage matrix homeostasis.

According to this aspect, the porosity and greater rigidity of the second phase as compared to the first is more suited for insertion within bone and provides a support, for the repair of osteochondral defects. The scaffolds of this invention are therefore, in some embodiments, ideally suited for incorporation within a defect site that spans two different types of tissue, i.e. bone and cartilage.

In some embodiments, the invention provides a scaffold for tissue repair, said scaffold consisting essentially of two phases wherein:
- a first phase of said two phases comprises solid coral or biolattice comprising hyaluronic acid and said first phase further comprises a series of hollows along a longitudinal axis in said first phase; and
- a second phase of said two phases comprises a solid coral or biolattice.

In some embodiments, according to this aspect, the first phase has a height of between 1-3 mm, or in some embodiments, 0.5-5 mm, or in some embodiments, 1-7 mm. In some embodiments, according to this aspect, hyaluronic acid is distributed preferentially within the hollows created within this phase. In some embodiments, a thin layer of hyaluronic acid may further form above the implant, which assumes a spongy exterior layer to the implant, at an apical region of the implant.

In some embodiments, the biocompatible polymer, such as hyaluronic acid is hydrophilic, and when synovial fluid comes into contact therewith at the apical layer above the scaffold, or when saline comes into contact therewith during the implantation procedure, the implant absorbs the fluid and reverts to a hydrogel, as opposed to the pre-implantation dehydrated/dessicated state. This reversion provides mechanical protection at the site of implantation, in some embodiments.

In some embodiments, the exterior layer, when "reconstituted" as described following implantation, may elute from the scaffold into the surrounding site and thereby participate in the stimulation or enhancement of repair at the site, including inter alia, serving as a chemoattractant for cells involved in the repair process.

According to this aspect, and in some embodiments, the first phase will further comprise a series of longitudinal holes. Such longitudinal holes may range from 15-60 holes placed throughout the phase along a longitudinal axis of the implant according to this aspect. In some embodiments, the holes or enlarged voids will have a diameter ranging from about 250-450 $\mu$m. In some embodiments, the holes or enlarged voids will have a diameter ranging from about 125-650 $\mu$m, or in some embodiments, ranging from about 175-550 $\mu$m.

According to this aspect, and in some embodiments, the series of holes or voids may be incorporated by physical manipulation of the implant, for example, and in some embodiments, solid aragonite or calcite may be isolated, cleaned and otherwise prepared as described herein, and a drill may be used to create the series of holes/voids as herein described. In some embodiments, other means, such as selective dissolution of the scaffolding material may be accomplished, where the selective dissolution along a longitudinal axis is accomplished by methods known in the art, including those described and exemplified herein.

According to this aspect, the second phase will contain solid coral or biolattice, which has not been further modified to alter the porosity of the phase, or in some embodiments, may be altered as described further hereinunder to specifically alter the pore volume or average pore diameter in the phase, whereby such modifications are substantially uniform throughout the phase.

Incorporation of a biocompatible polymer such as hyaluronic acid in the first phase of the implant may be accomplished via any means, including pressure-driven application, for example, via application under vacuum, centrifugal force or mechanical pressure. In some embodiments, gravitational force is sufficient to allow appropriate and relatively homogenous penetration of the hyaluronic acid to a desired depth of the implant, creating the first phase as herein described. According to this aspect, in one embodiment, visual inspection of the implant, for example using the staining with Fast Green/Safranin O, demonstrates uniform distribution of the hyaluronic acid through the phase and to a desired depth as a function of the time and conditions of application.

According to this aspect, and in some embodiments, when applying the scaffolds to a site of bone and/or cartilage repair, or in some embodiments, to a defect site where both bone and cartilage are affected and in need of repair and/or regeneration, the skilled artisan will appreciate that the second phase of the scaffold is inserted within the bone defect site whereas the first phase is inserted within the cartilage defect site.

In some embodiments, such scaffolds may be administered to a subject with a bone defect in need of repair, wherein access to the bone defect results in the creation of a defect in the overlying cartilage, and the scaffolds of this invention allow for the healing of both affected tissues. In other embodiments, such scaffolds may be administered to a subject with a cartilage defect in need of repair, wherein optimal insertion of the scaffold for stimulation of cartilage repair necessitates anchoring of the scaffold in the underlying bone, for example, by creating a minimal void in the underlying bone for insertion of the scaffold, and once inserted, the scaffold facilitates repair of both the overlying cartilage and underlying bone.

In other embodiments, such scaffolds may be administered to a subject with an osteochondral defect, where both bone and cartilage tissue are in need of repair as part of the pathogenesis of the disorder. The scaffolds according to this aspect are, in some embodiments, particularly suited for such applications.

This invention also provides for the unexpected application that cartilage and/or bone regeneration, repair and enhancement of formation is optimal when the coral scaffolding comprises at least two phases, which phases comprise voids, and vary in terms of the average diameter of the voids within each phase, and/or that cartilage and/or bone regeneration, repair and enhancement of formation is optimal when the coral scaffolding comprises at least two phases, which phases vary in terms of their respective pore volumes (porosity).

It will be appreciated that the term "coral" will refer to a starting material from which aragonite and/or calcite may be isolated.

In one embodiment, the present invention provides a scaffold for inducing or enhancing cartilage or bone regeneration, repair, enhancement of formation, or a combination thereof, which scaffold consists of a solid form of aragonite or calcite and further comprises:
- at least a first phase, comprising voids having an average diameter ranging from about 60-160 $\mu$m; and
- at least a second phase, comprising voids having an average diameter ranging from about 170-850 $\mu$m.

It will be appreciated that according to this aspect, the term "first phase" and "second phase" do not apply to a particular order with respect to insertion of the phase within an osteochondral defect, and either the first phase or the second phase may be oriented to be proximal to cartilage within a repair site, as opposed to the prior embodiment of a scaffold as described hereinabove, wherein the first phase is inserted proximal to a site of cartilage repair. According to this aspect, the scaffold may be further modified to comprise both the indicated void average diameter, and either phase may further comprise a biocompatible polymer such as hyaluronic acid and a series of voids or holes along a longitudinal axis of said phase, wherein the biocompatible polymer such as hyaluronic acid is located substantially within such series of voids or holes.

In some embodiments, the term "solid form" with respect to aragonite, refers to solid aragonite harvested from coral, which aragonite is treated to remove debris, proteins and other particulate matter, however, such coral-derived materials are not hydrothermically transformed, nor ground, and resuspended.

In some embodiments, the coral for use in the preparation of the scaffolds of this invention may be processed by any means known in the art, for example, as described in PCT International Application Serial No. PCT/IL2009/000828, which is incorporated by reference as if fully set forth herein. In some embodiments, the coral may be processed according to a process of this invention.

In some embodiments, this invention provides a process for the purification of a coralline-based scaffolding, said process comprising the steps of:
- contacting solid aragonite of a desired size and shape with a solution comprising an oxidizing agent; and
- washing and drying said solid aragonite whereby one or each of said steps is conducted under applied negative pressure.

According to this aspect, and in some embodiments, the applied negative pressure ranges between about 0.2 to 0.00001 Bar, or in some embodiments, the applied negative pressure ranges between 0.4 to 0.0000001 Bar.

According to this aspect, and in some embodiments, the oxidizing agent for use in the processes of this invention may be any suitable oxidizing agent, which facilitates the removal of organic debris from coralline-based scaffolds.

In some embodiments, the oxidizing agent may include, inter alia, potassium nitrate (KNO3), hypochlorite and other hypohalite compounds, iodine and other halogens, chlorite, chlorate, perchlorate, permanganate salts, ammonium cerium (IV) nitrate, hexavalent chromium compounds, pyridinium chlorochromate (PCC), and chromate/dichromate compounds, peroxide compounds, sulfoxides, persulfuric acid, or nitric acid, acetone, ammonium peroxydisulfate, 1,4-benzoquinone, N-tert-butylbenzensulfinilmidoyl, chloride, tert-butyl hydroperoxide, tert-butyl hypochlorite, 3-chloroperoxybenzoic acid, meta-chloroperbenzoic acid, cumene hydroperoxide, dimethyl sulfoxide, hydrogen peroxide, manganese oxide, meta-chloroperbenzoic acid, N-methylmorpholine-N-oxide, methyltrioxorhenium (MTO), oxalyl chloride, N-tert-butylbenzenesulfinimidoyl chloride, oxone, oxygen, ozone, peracetic acid, periodic acid, peroxy acid, pivaldehyde, potassium permanganate, potassium peroxydisulfate, potassium peroximonosulfate, 2-propanone, sodium chlorite, sodium percarbonate, sodium periodate, styrene, trichloroisocyanuric acid (TCCA), 2,2,6,6-tetramethylpiperidinyloxy TEMPO, tert-butyl hydroperoxide, tert-butyl hypochlorite, tetrabutylammonium peroxydisulphate, trimethylacetaldehyde. In some embodiments, the oxidizing agent is sodium hypochlorite.

According to this aspect, and in some embodiments, the process comprises conducting said contacting under mildly acidic conditions.

According to this aspect, and in some embodiments, the process comprises subjecting the solid aragonite to a temperature of at least 275° C. under applied negative pressure.

According to this aspect of the invention, the process comprises contacting the aragonite with an oxidizing agent under applied negative pressure, washing and drying the aragonite applied negative pressure, or both steps are conducted under applied negative pressure. The applied negative pressure ranges between 0.2 to 0.00001 Bar, or in some embodiments, between about 0.4 to 0.0000001 Bar, according to this aspect of the invention.

The scaffolds, kits, processes and methods of this invention make use of solid coralline forms.

The solid forms or scaffolds of this invention may be of aragonite or calcite origin.

In some embodiments, the term "solid form" with respect to calcite refers to calcite isolated from coral, which calcite is treated to remove debris, proteins and other particulate matter, however, such materials are not hydrothermically transformed, nor ground, and resuspended. In some embodiments, the "solid form" calcite refers to calcite obtained by the preparation of an aragonite solid form, which form is then converted to calcite by known methods in the art, for example by exposing the form to high temperature under vacuum.

Any method for conversion of aragonite to calcite as known in the art may be used to prepare calcite scaffolds of this invention.

The scaffolding of this invention comprises, in some embodiments, a series of voids, and the at least two phases present in the scaffolding of this invention vary in terms of the average diameter of the voids present in each phase. In some embodiments, the scaffold will comprise at least a first phase, comprising voids having an average diameter ranging from about 60-460 μm. In some embodiments, the first phase comprises voids having an average diameter ranging from about 60-90 μm, or in some embodiments, from about 80-130 μm, or in some embodiments, from about 120-160 μm.

In some embodiments, the scaffold will comprise at least a second phase, comprising voids having an average diameter ranging from about 170-850 μm. In some embodiments, the second phase comprises voids having an average diameter ranging from about 170-400 μm, or in some embodiments, from about 250-500 μm, or in some embodiments, from about 450-700 μm or in some embodiments, from about 550-850 μm In some embodiments, according to this aspect, the scaffold further comprises a third phase, comprising voids having an average diameter ranging from about 150-300 μm and said second phase comprises voids having an average diameter ranging from about 350-850 μm and said third phase is positioned between said first and second phase. In some embodiments, such at least third phases may be referred to herein interchangeably as an "intermediate phase".

In some embodiments, the scaffold is cylindrical in shape and has a diameter of about 5-15 mm, and a height of about 5-25 mm. In some embodiments, the scaffold has a diameter of about 1-35 mm, and a height of about 1-45 mm, or about 5-40 mm, and a height of about 5-60 mm, or about 5-15 mm, and a height of about 5-45 mm.

The average diameter of the voids within the phases of the scaffolding of this invention may be determined by any means, including digital images analysis, as exemplified further hereinbelow. In one embodiment, a coral for use in a scaffold of this invention comprises an average void diameter appropriate for cell seeding and/or development of vasculature.

The solid forms of this invention comprise at least two phases, which phases contain pores, owing to the porous nature of the materials of which the scaffolding is comprised. In some embodiments, the phases vary in terms of the pore volume (porosity) of each phase.

In one embodiment, the invention provides a scaffold for the repair of cartilage, which scaffold consists of a solid form of aragonite or calcite and further comprises:
- at least a first phase, comprising pores having a pore volume ranging from about 35-55%; and
- at least a second phase, comprising pores having a pore volume ranging from about 56-95%

It will be appreciated that according to this aspect, the term "first phase" and "second phase" do not apply to a particular order with respect to insertion of the phase within a defect site, for example, within an osteochondral defect, and either the first phase or the second phase may be oriented to be proximal to, for example, the cartilage within a repair site, as opposed to the prior embodiment of a scaffold as described hereinabove, wherein the first phase is inserted proximal to a site of cartilage repair. According to this aspect, the scaffold may be further modified to comprise phases comprising pores having the indicated pore volume, and either phase may further comprise a biocompatible polymer such as hyaluronic acid and a series of voids or holes along a longitudinal axis of said phase, wherein the biocompatible polymer such as hyaluronic acid is located substantially within such series of voids or holes.

As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials.; 26(27):5474-91, which is hereby incorporated by reference in its entirety.

In some embodiments, according to this aspect, the scaffold comprises at least a first phase, comprising pores having a pore volume ranging from about 35-45% and in some embodiments, the scaffold comprises a first phase comprising pores having a pore volume ranging from about 40-55%.

In some embodiments, according to this aspect, the scaffold comprises at least a second phase, comprising pores having a pore volume ranging from about 56-70% and in some embodiments, ranging from about 60-74% or the scaffold comprises a second phase comprising pores having a pore volume ranging from about 65-75%, or in some embodiments, ranging from about 70-85%, or in some embodiments, ranging from about 80-95%.

In some embodiments, according to this aspect, the scaffold further comprises a third phase, comprising pores having a pore volume ranging from about 80-95%, wherein said second phase comprises voids having an average diameter ranging from about 56-80% and said second phase is positioned between said first and third phase.

In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In some embodiments, the invention provides a scaffold for the repair, regeneration or enhancement of formation of cartilage, bone, or a combination thereof, which scaffold consists of a solid form of aragonite or calcite isolated from a coral and further comprises:
    at least a first phase, comprising voids having an average diameter, pore volume or combination thereof, which corresponds to that of the native coral from which said solid form was isolated; and
    at least a second phase, comprising voids having an average diameter, pore volume or combination thereof, which average void diameter, pore volume or combination thereof is greater than that of said first phase by from about 15-100%.

It will be appreciated that according to this aspect, the term "first phase" and "second phase" do not apply to a particular order with respect to insertion of the phase within a defect site, for example, within an osteochondral defect, and either the first phase or the second phase may be oriented to be proximal to, for example, the cartilage within a repair site, as opposed to the prior embodiment of a scaffold as described hereinabove, wherein the first phase is inserted proximal to a site of cartilage repair. According to this aspect, the scaffold may be further modified to comprise phases comprising pores having the indicated pore volume, or voids having the indicated average diameter, or combinations thereof and either phase may further comprise a biocompatible polymer such as hyaluronic acid and a series of voids or holes along a longitudinal axis of said phase, wherein the biocompatible polymer such as hyaluronic acid is located substantially within such series of voids or holes.

In some embodiments, according to this aspect, the scaffold comprises voids having an average diameter, pore volume or combination thereof, which average pore diameter, pore volume or combination thereof is greater than that of said first phase by from about from about 15-35% and in some embodiments, ranging from about 60-74% or the scaffold comprises a second phase comprising pores having a pore volume ranging from about 45-65%, or in some embodiments, ranging from about 50-85%, or in some embodiments, ranging from about 80-95%

In some embodiments, the invention provides a scaffold for the repair, regeneration or enhancement of formation of cartilage, bone, or a combination thereof, which scaffold consists of a solid form of aragonite or calcite isolated from a coral and further comprises:
    at least a first phase, comprising voids having an average diameter, pore volume or combination thereof, which corresponds to that of the native coral from which said solid form was isolated; and
    at least a second phase, comprising voids having an average diameter, pore volume or combination thereof, which average void diameter, pore volume or combination thereof is greater than that of said first phase by from about 15-900%.

It will be appreciated that according to this aspect, the term "first phase" and "second phase" do not apply to a particular order with respect to insertion of the phase within a defect site, for example, within an osteochondral defect, and either the first phase or the second phase may be oriented to be proximal to, for example, the cartilage within a repair site, as opposed to the prior embodiment of a scaffold as described hereinabove, wherein the first phase is inserted proximal to a site of cartilage repair. According to this aspect, the scaffold may be further modified to comprise phases comprising pores having the indicated pore volume, or voids having the indicated average diameter, or combinations thereof and either phase may further comprise a biocompatible polymer such as hyaluronic acid and a series of voids or holes along a longitudinal axis of said phase, wherein the biocompatible polymer such as hyaluronic acid is located substantially within such series of voids or holes.

In some embodiments, according to this aspect, the scaffold comprises a second and third phase having voids having an average diameter, pore volume or combination thereof, which average pore diameter, pore volume or combination thereof is greater than that of said first phase by from about from about 15-900% wherein, in some embodiments, the third phase comprises voids having an average diameter, pore volume or combination thereof ranging from about 300-900%, or in some embodiments, 300-450%, or in some embodiments, 425-600%, or in some embodiments, 575-900% and the scaffold comprises a second phase comprises voids having an average diameter, pore volume or combination thereof ranging from about ranging from about 15-200%, or in some embodiments, 50-125%, or in some embodiments, 125-200%, of that which is in the first phase.

According to this aspect, and in on embodiment, the scaffold will comprise a third phase, comprising voids having an average diameter, pore volume or combination thereof, which average pore diameter, pore volume or combination thereof is greater than that of said first phase by from about 15-35% and said second phase comprises voids having an average diameter, pore volume or combination thereof, which average pore diameter, pore volume or combination thereof is greater than that of said first phase by from about 40-100% and said third phase is positioned between said first and second phase.

It will be appreciated that different species of coral vary in terms of their average pore diameter and pore volume and the invention contemplates use of any such coral as a starting material for the preparation of the scaffolds as herein described, where the scaffold is characterized in that it possesses at least two phases, wherein a first phase contains voids, and a pore volume native to the coral from which the scaffolds are prepared, and a second phase, whose voids are enlarged, whose overall pore volume increases, or a combination thereof.

In one embodiment, this invention provides a scaffold for repair of cartilage comprising a biolattice consisting essentially of calcite capable of being inserted within a site of cartilage repair. In some embodiments, the biolattice is derived from *Tetraclita rufotincta*.

The term biolattice refers to a CaCO3-containing biomaterial which is crystalline or amorphous and derived from, inter alia, a coral or barnacle species.

Calcite polymorphs of calcium carbonate from natural limestone have been described {Fujita Y, Yamamuro T, Nakamura T, Kotani S, Ohtsuki C, Kokubo T. J Bimed Mater Res. 1991 August;25(8):991-1003}. In vitro transformation of calcite by heating aragonite isolated from natural coral, has been described as well (Fricain J C, Bareille R, Ulysse F, Dupuy B, Amedee J. J. Biomed Mater Res. 1998 October;42(1):96-102);

In another embodiment, this invention provides a scaffold for tissue repair, said scaffold comprising at least two phases wherein a first phase of said two phases comprises a coral or biolattice and a second phase comprises a biocompatible polymer or polymers.

In one embodiment, the term "proximal" refers to something being situated close to a particular locale. In one embodiment, a scaffold of this invention is forcibly held in position within a site of cartilage repair by a raised region of the scaffold contacting tissue situated at or proximal to a site of cartilage repair.

By optimizing the specific positioning of a scaffold the porous crystalline structure of a coral scaffolds of this invention, described below, is accessible to beneficial components located within a tissue milieu. For example, the porous crystalline structure of coral allows in-growth of blood vessels to create a blood supply for the cartilage that will infiltrate the scaffold during cartilage repair. By penetrating into a bone marrow void, mesenchymal stem cells located within the bone marrow now have access to the exposed surface of the scaffold. In one embodiment, the region of the scaffold penetrating into a bone marrow void attracts mesenchymal stem cells from the bone marrow and promotes blood vessel formation to the site of cartilage repair. In one embodiment, the region of the scaffold penetrating into a bone marrow void promotes adhesion, proliferation, or differentiation or a combination thereof, of the mesenchymal stem cells attracted to the scaffold.

Thus, it will be apparent to one skilled in the art that the specific positioning of the scaffold within a site of cartilage repair arranges the scaffold of this invention such that the scaffold is most effective for cartilage repair.

In some embodiments, the region of the scaffold which penetrates through bone and stably inserts within bone marrow is also the region of the scaffold which positions and confines the scaffold within a site of cartilage repair, or in some embodiments, the region of the scaffold which penetrates through bone and stably inserts within bone marrow is not the region which positions and confines the scaffold within a site of cartilage repair. In one embodiment, the region inserts in such a way that no other portion of the scaffold is in contact with tissue at the site. In another embodiment, the region inserts in such a way that the side walls of the scaffold make contact with tissue at the site of cartilage repair.

In some embodiments, the scaffold is of a shape which accommodates a site of repair.

In some embodiments, the scaffold approximates the form of a cylinder, cone, tac, pin, screw, rectangular bar, plate, disc, pyramid, granule, ball or cube.

In some embodiments, the scaffolds of this invention may be used in conjunction with other known and/or available materials for stimulating/enhancing bone and/or cartilage repair. In some embodiments, the scaffolds of this invention may be utilized to affix additional scaffolds, for example for use in whole joint repair or ligament repair, or other connector tissue repair.

In some embodiments, the scaffolds of this invention may be used for example, as a pin, in conjunction with other scaffolds for bone repair or regeneration, etc. It is to be understood that any use of the scaffolds of this invention, alone or in conjunction with other appropriate materials, for the treatment, repair or stimulation of growth of bone and/or cartilage is to be considered as part of this invention It will be appreciated that the scaffolds of this invention may be of any suitable shape or size to accommodate its application in accordance with the methods of this invention. For example, and in some embodiments, for applications of the scaffolds of this invention within long bones of a subject, the dimensions of the scaffold will be scaled to approximate that of the site into which the scaffold will be implanted, and may be on an order of magnitude scaling from millimeters to centimeters, as needed. Similarly, shapes of the scaffolds of the invention may be any shape into which the scaffolds of this invention may be machined or processed, and may have any configuration as will be appropriate to achieve the desired growth, repair or regeneration of bone and/or cartilage.

In some embodiments, the scaffold comprises a hollow or hollows along a Cartesian coordinate axis of said scaffold and in some embodiments, the axis is a long axis of said scaffold.

In some embodiments, the invention provides a kit for the repair, regeneration or enhancement of formation of cartilage, bone, or a combination thereof comprising the scaffold of this invention, directions for utilizing said scaffold in the repair, regeneration or enhancement of formation of cartilage, bone, or a combination thereof and optionally a tool or tools for optimal insertion of said scaffold, seeding said scaffold with cells or a combination thereof.

In one embodiment, the coral is seeded with a precursor cell. In one embodiment, the precursor cell is a mesenchymal stem cell. In other embodiments, the cell may be a mesenchymal cell; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized.

In some embodiments, the scaffold comprises a third phase comprising a coral which differs in composition from said first phase.

In some embodiments, the third phase is positioned between said first phase and said second phase.

In some embodiments, the third phase is positioned proximally to said first phase and distally to said second phase.

In some embodiments, the third phase is positioned proximally to said second phase and distally to said first phase.

In some embodiments, the first phase or said second phase is inserted into a region which is proximal to subchondral bone.

In some embodiments, the scaffold may comprise a third phase, which may be inserted into a region which is proximal to subchondral bone.

In some embodiments, the phase which is inserted comprises at least a terminal modification, which enhance the tissue repair In one embodiment, a site of cartilage repair may be considered to comprise a 3 dimensional (3-D) space at or proximal to a site of a cartilage and/or defect or potential. defect. In one embodiment, this 3-D space comprises at least a wall or a floor, or a combination thereof, and positioning within such a site may be described herein, relative to said wall or floor, or in some embodiments, positioning may be relative to insertion within a tissue site proximal to said wall or floor. In some embodiments, positioning include insertion of the scaffold or a region thereof, past the wall and/or floor of cartilage and/or bone tissue or a site of defect or injury or potential defect or injury in the cartilage and/or bone tissue, such that insertion into bone tissue occurs.

One skilled in the art will recognize that the shape of a site of cartilage and/or bone repair and the shape of a 3-D scaffold of this invention provide many different combinations for stably positioning a scaffold within a site of cartilage repair and/or bone. In one embodiment, a scaffold of this invention is shaped prior to use in methods of this invention for cartilage repair and/or bone. In one embodiment, a scaffold of this invention is shaped concurrent to use in methods of this invention for cartilage and/or bone repair. By shaping a scaffold concurrent with use of the scaffold in methods of this invention, the dimensions of the scaffold may be precisely selected for specific positioning of the scaffold within a site of repair. It will be appreciated that multiple scaffolds of this invention may be placed within or shaped and placed within a site of cartilage and/or bone repair.

In some embodiments, reference to a "scaffold", "implant" or "plug", as used herein refers to any embodiment or combined embodiments as herein described with regard to the scaffolds to be considered as being included in the described aspect of this invention. For example, reference to a "scaffold" as used herein, is to be understood to refer to any embodiment of a scaffold as described herein being applicable for the indicated purpose or containing the indicated attribute, etc.

In one embodiment, "scaffold" refers to a shaped platform used for cartilage and/or bone repair, wherein the shaped platform provides a site for cartilage and/or bone regeneration. In one embodiment, the scaffold is a temporary platform. In one embodiment, "temporary platform" refers to a natural degradation of a coral of this invention that occurs over time during cartilage and/or bone repair, wherein the natural fully or partially degradation of the coral may results in a change of scaffold shape over time and/or change in scaffold size over time.

In one embodiment, the coral is shaped in the form of the tissue to be grown. For example, the coral can be shaped as a piece of cartilaginous tissue, such as a meniscus for a knee or elbow; a joint; an articular surface of a bone, the rib cage, a hip, a pelvis, an ear, a nose, a ligament, the bronchial tubes and the intervertebral discs.

This invention provides, in some embodiments, coral scaffolds for use in repairing cartilage and/or bone tissue defects associated with physical trauma, or cartilage and/or bone tissue defects associated with a disease or disorder in a subject.

In one embodiment of this invention, the term "coral" refers to coral which is cut from a single piece of coral. In one embodiment, the coral has pore-like cavities or interstices.

In one embodiment, the coral scaffold is shaped prior to use in a method of cartilage and/or bone repair. In one embodiment, the coral scaffold is shaped concurrent with a method of cartilage and/or bone repair, e.g., the coral scaffold may be shaped during surgery when the site of repair may be best observed, thus optimizing the shape of the scaffold used.

In one embodiment, the scaffolds, methods and/or kits of this invention employ use of a coral. In one embodiment, the coral comprise any species, including, inter alia, *Porites, Acropora, Millepora*, or a combination thereof.

In one embodiment, the coral is from the *Porites* species. In one embodiment, the coral is *Porites Lutea*. In most species, the void to solid ratios is generally in the range of 0.4 to 0.6, and the void phase completely interconnects, forming a highly regular network that interpenetrates the solid calcium carbonate phase. In one embodiment, this uniform and interconnecting architecture is particularly useful as a framework in the scaffolds, methods and/or kits of this invention.

In one embodiment, the coral is from the *Acropora* species. In one embodiment, the coral is *Acropora grandis*, which in one embodiment is very common, fast growing, and easy to grow in culture. Thus, in one embodiment Acropora samples can be easily collected in sheltered areas of the coral reefs and collection from the coral reefs can be avoided by use of cultured coral material.

The average skeletal density of *Acropora grandis* is 2.7 g/ml. Because the skeleton of this coral species is dense and strong, it can be easily machined to a variety of configurations of shaped products or structures of different sizes, for example by grinding. This material is particularly suited for use in an implant device, in particular for weight-bearing joints such as knee and hip joints, where strength is an essential property of the implant device. Thus, in one embodiment, *Acropora coral* is useful as a framework in the scaffolds, methods and/or kits of this invention.

In another embodiment, the coral is from the *Millepora* species. In one embodiment, the coral is *Millepora*

*dichotoma*. In one embodiment, the coral has a pore size of 150 μm and can be cloned and cultured, making *Millerpora* useful as a framework in the scaffolds, methods and/or kits of this invention.

In another embodiment, the coral is from any one or more of the following species: *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danailike"; *Acropora divaricata; Acropora donei; Acropora echinata; Acropora efflorescens; Acropora gemmifera; Acropora globiceps; Acropora granulosa; Acropora cf hemprichi; Acropora kosurini; Acropora cf loisettae; Acropora longicyathus; Acropora loripes; Acropora cf lutkeni; Acropora paniculata; Acropora proximalis; Acropora rudis; Acropora selago; Acropora solitaryensis; Acropora cf spicifera* as per Veron; *Acropora cf spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia cf echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora cf vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia cf lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata;* or any coral known in the art, or a combination thereof.

In another embodiment, coral for use in the scaffolds, methods and/or kits of this invention may be *Madreporaria, Helioporida* of the order Coenothecalia, *Tubipora* of the order Stolonifera, *Millepora* of the order Milleporina, or others known in the art. In some embodiments, coral for use in the scaffolds, methods and/or kits of this invention may comprise scleractinian coral, including in some embodiments, Goniopora and others. In some embodiments, coral for use in the scaffolds, methods and/or kits of this invention may comprise Alveoppora. In some embodiments, coral for use in the scaffolds, methods and/or kits of this invention may comprise bamboo corals, including in some embodiments, coral from the family Isididae, genera Keratoisis, Isidella, and others.

As described above, a scaffold's region's ability to position and confine the scaffold of this invention is dependent on the region's geometry and the geometry at the site of cartilage and/or bone repair where the scaffold will be implanted. In one embodiment, the region's geometry comprises a sharp edge. In one embodiment, the region's geometry comprises a rounded edge. In one embodiment, the region's geometry comprises a jagged edge.

In one embodiment of this invention, an optimal depth and angle within a site of cartilage and/or bone repair comprise the depth and angle most beneficial for cartilage and/or bone repair. In one embodiment, the optimal depth and angle most beneficial comprise a position so that a scaffold of this invention is accessible to a pool of mesenchymal stem cells, a tissue milieu, blood vessels, nutrients, an effector compound, or a therapeutic compound, or a combination thereof.

In one embodiment of this invention, the term "depth" refers to a measurement of a scaffold of this invention extending from an imaginary line resting on the open surface of a repair site to a place beneath the tissue floor at a site of cartilage and/or bone repair.

It will be recognized by one skilled in the art that the depth of other regions of the scaffold may not be below any tissue surface. For example, and in an embodiment of this invention, based on a site of cartilage repair shaped like a cylindrical pit, an imaginary line drawn to rest across the opening of the pit represents the top of the pit. In one embodiment, positioning of the scaffold results in the entirety of the scaffold being below the top of the pit and therefore at a depth below the imaginary line across the opening. In one embodiment, positioning of the scaffold results in a portion of the scaffold being above the top of the pit and therefore not wholly within a site of cartilage repair. The benefit of placing a scaffold at a given depth may depend on the resulting contact the scaffold makes with surrounding tissue, either within the site of cartilage repair or proximal to the site of cartilage repair.

Similarly, and in another aspect of the invention, with regard to implantation of the scaffolds of this invention within bone, the site of implantation may as well be envisioned as a pit, with an imaginary line drawn to rest across the opening of the pit, representing the top of the pit. According to this aspect, positioning of the scaffold results in the entirety of the scaffold being below the top of the pit or in some embodiments, positioning of the scaffold may result in a portion of the scaffold being above the top of the pit and therefore not wholly within the site of bone repair. The benefit of placing a scaffold at a given depth may depend on the resulting contact the scaffold makes with surrounding tissue, either within the site of bone repair or proximal to the site of bone repair.

In one embodiment, the term "angle" refers to a measurement of the arc formed by an imaginary line along the long axis of the scaffold and an imaginary plumb line perpendicular to the line resting at the opening of a site of cartilage and/or bone repair described above, with the arc progressing in a clockwise direction around this imaginary plumb line. Thus, in one embodiment a scaffold of this invention may be positioned and confined at an optimal depth and angle such that the scaffold is parallel to the perpendicular line, and therefore the angle would be 0 degrees. In one embodiment a scaffold of this invention may be positioned perpendicular to the imaginary plumb line, and therefore the angle would be 90 degrees. In one embodiment, the scaffold is positioned and confined at an angle equaling or less than 10 degrees. In one embodiment, the scaffold is positioned and confined at an angle equaling or less than 35 degrees. In one embodiment, the scaffold is positioned and confined at an angle equaling or less than 55 degrees. In one embodiment, the scaffold is positioned and confined at an angle equaling or less than 75 degrees. In one embodiment, the scaffold is positioned and confined at an angle equaling or less than 95 degrees. In one embodiment, the scaffold is positioned and confined at an angle equaling or less than 115 degrees. In one embodiment, the scaffold is positioned and confined at an angle equaling or less than 125 degrees. In one embodiment, the scaffold is positioned and confined at an angle of less than 145 degrees. In one embodiment, the scaffold is positioned and confined at an angle equaling or less than 165 degrees. In one embodiment, the scaffold is positioned and confined at an angle less than 180 degrees In some embodiments, multiple scaffolds are inserted to maximally occupy a defect site, such that each scaffold material may be inserted at a different angle and/or shape and/or depth and/or porosity to accommodate proper insertion into the desired region within a site of cartilage and/or bone repair. It is to be understood that the reference to angles of positioning above may be with regard to one or more scaffolds inserted in a particular cartilage and/or bone defect site.

Contact between exposed surfaces of a scaffold and tissue at or proximal to a site of cartilage and/or bone repair provides a bioactive surface which, in the methods of use of this invention may induce or enhance cartilage and/or bone repair. For example, in one embodiment, the exposed surface of a scaffold provides a bioactive surface attracting mesenchymal stem cells. In another embodiment, the exposed surface provides a place for mesenchymal stem cell attachment, growth, proliferation, or differentiation, or a combination thereof, all processes which induce or enhance cartilage repair. In addition, the exposed surface of a scaffold may attract blood vessels. Moreover, tissue at or proximal to a site of cartilage and/or bone repair may be a rich source of nutrients, effector compounds, therapeutic compounds, or a combination thereof, which may be beneficial in cartilage and/or bone repair so that contact between an exposed surface of a scaffold and such tissue induces or enhances cartilage and/or bone repair.

In one embodiment, the angle of placement of a scaffold is such that the scaffold is in contact with a region of a wall within a site of cartilage and/or bone repair. In one embodiment, a scaffold of this invention may be positioned and confined such that there is maximal contact between the scaffold and tissues at or proximal to a site of cartilage and/or bone repair. In one embodiment, a scaffold of this invention may be positioned and confined such that a region of the scaffold penetrates a subchondral bone and/or bone marrow void and there is maximal contact between the scaffold and tissues at or proximal to a site of cartilage and/or bone repair. In one embodiment, contact between the exposed surface of the scaffold and the tissue at or proximal to a site of cartilage and/or bone repair provides maximal surface area of the scaffold for interaction with a population of mesenchymal stem cells, blood vessels, effector compounds, or other components of a tissue milieu, or a combination thereof.

A scaffold of this invention may comprise multiple raised portions. It is possible for different portions of a scaffold to serve different functions. For example, in one embodiment a raised portion of a scaffold may hold the scaffold in place within a site of cartilage and/or bone repair, or a raised portion of a scaffold may function as an exposed surface for attraction, growth, proliferation or differentiation of mesenchymal stem cells, or a raised portion of a scaffold may function to fit a tool of this invention, or any combination thereof.

In one embodiment, 100% of multiple raised portions specifically positions and confines a coral. In one embodiment, at least 80% of multiple raised portions specifically positions and confines a coral. In one embodiment, at least 60% of multiple raised portions specifically positions and confines a coral. In one embodiment, at least 40% of multiple raised portions specifically positions and confines a coral. In one embodiment, at least 20% of multiple raised portions specifically positions and confines a coral. In one embodiment, at least 10% of multiple raised portions specifically positions and confines a coral. In one embodiment, at least 1% of multiple raised portions specifically positions and confines a coral.

In one embodiment, placing and confining a scaffold of this invention at an optimal depth and angle within a site of cartilage and/or bone repair provides for penetration of a portion of the exposed surface of the scaffold, through a bone tissue.

By optimizing the specific positioning of a scaffold the porous crystalline structure of the scaffolds of this invention, described below, is accessible to beneficial components located within a tissue milieu. For example, the porous crystalline structure of the scaffold allows in-growth of blood vessels to create a blood supply for the cartilage and/or bone that will infiltrate the scaffold during cartilage and/or bone repair. In one embodiment, the scaffold attracts mesenchymal stem cells and promotes blood vessel formation to the site of cartilage repair.

Thus, it will be apparent to one skilled in the art that the specific positioning of the scaffold within a site of cartilage and/or bone repair arranges the scaffold of this invention such that the scaffold is most effective for cartilage and/or bone repair.

In one embodiment, "scaffold" refers to a shaped platform used for cartilage and/or bone repair, wherein the shaped platform provides a site for cartilage and/or bone formation and/or regeneration. In one embodiment, the scaffold is a temporary platform. In one embodiment, "temporary platform" refers to a natural fully or partially degradation of a coral of this invention that occurs over time during cartilage repair, wherein the natural degradation of the coral may results in a change of scaffold shape over time and/or a change in scaffold size over time.

In one embodiment, the coral is shaped in the form of the tissue to be grown. For example, the coral can be shaped as a piece of cartilaginous or bony tissue, such as a meniscus for a knee or elbow; a joint; an articular surface of a bone, the rib cage, a hip, a pelvis, an ear, a nose, the bronchial tubes, the intervertebral discs, a ligament, a vertebra, the tibia, the femur, the shoulder and the jaw.

This invention provides, in some embodiments, coral scaffolds for use in repairing cartilage and/or bone tissue defects associated with physical trauma, or cartilage and/or bone tissue defects associated with a disease or disorder in a subject.

In one embodiment of this invention, the term "coral" refers to coral which is cut from a single piece of coral. In one embodiment, the coral has pore-like cavities or interstices.

In one embodiment, the coral scaffold is shaped prior to use in a method of cartilage and/or bone repair. In one embodiment, the coral scaffold is shaped concurrent with a method of cartilage and/or bone repair, e.g., the coral scaffold may be shaped during surgery when the site of repair may be best observed, thus optimizing the shape of the scaffold used.

In one embodiment, the size of a scaffold may be any size that would be useful for the purposes of the present invention, as would be known to one skilled in the art. In one embodiment, the scaffold or a portion thereof may be about the size of a site of cartilage and/or bone repair. In one embodiment, the scaffold or a portion thereof may be about the size of a cartilage and/or bone defect so that the scaffold may be placed within a site of cartilage and/or bone repair. In another embodiment, the scaffold may be larger than the size of a cartilage and/or bone defect. For example, in one embodiment, the scaffold of this invention may be larger than the size of a cartilage and/or bone defect, whereby the scaffold may extend to a site of mesenchymal cell availability. In one embodiment, the scaffold may be smaller than the size of a cartilage and/or bone defect.

In some embodiments, the scaffold size will be on a millimeter scale, for example, having at least one long axis of about 2-200 mm, or in some embodiments, about 1-18 mm, or in some embodiments, about 0.5 mm-3 mm, or in some embodiments, about 6-12 mm, or in some embodiments, about 10-15 mm, or in some embodiments, about 12-40 mm, or in some embodiments, about 30-100 mm, or in some embodiments, about 50-150 mm, or in some embodiments, about 100-200 mm.

In some embodiments the scaffold size will be on the centimeter scale, for example having at least one long axis of about 0.5-30 cm In one embodiment, the scaffold may be about the same size as a tissue void at a site of tissue repair. This tissue void may be due to a cartilage and/or bone defect, cartilage and/or bone degeneration or may have been created artificially during methods of cartilage and/or bone repair or any combination thereof. In one embodiment, the tissue void comprises an absence of cartilage and/or bone tissue. In one embodiment, the scaffold or a portion thereof may be the size of a cartilage and/or bone defect such that the scaffold may be placed within a site of cartilage and/or bone repair to enhance cartilage and/or bone formation at the site of cartilage and/or bone repair. In another embodiment, the scaffold may be larger than the size of a cartilage and/or bone defect so that the scaffold may reach to a site of mesenchymal stem cell availability.

Figure 11A:
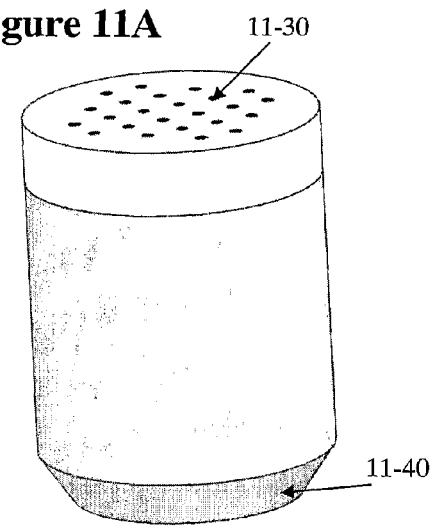
FIGS. 11A-C depict embodiments of scaffolds/implants of this invention. According to this aspect, one phase comprises aragonite with a series of holes or voids along a longitudinal axis (11-30) and is impregnated with Hyaluronic acid (11-10), and another phase comprises only aragonite (11-20). The terminus of the scaffold according to this aspect, is tapered (11-40) for ease of insertion as a tight fit, within a site of osteochondral repair.
Figure 11B:
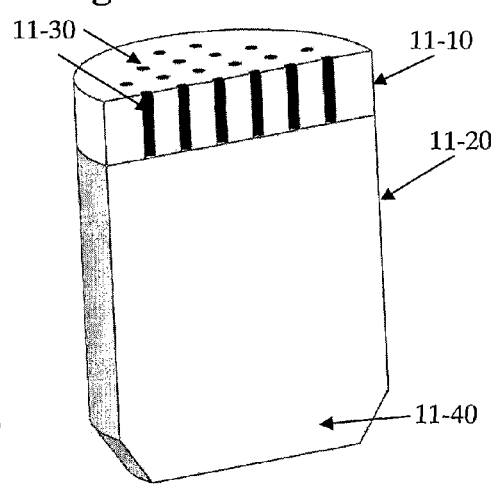
Figure 11C:
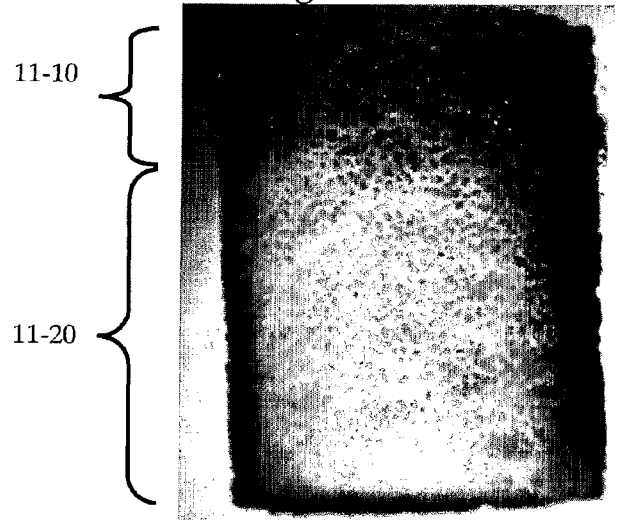

In some embodiments, a tight fit is desirable with regard to fitting the implant within the site of tissue repair. According to this aspect, and in some embodiments, it may be desirable to taper a terminus of the scaffolds of this invention for easy insertion within a tight space for optimal tight fitting of the implant. FIG. 11 for example, shows a schematic of an embodied scaffold of this invention, whereby the terminus inserting into bone, in the second phase of the scaffold is tapered (11-40) to accommodate an easier tight fit.

In one embodiment of this invention, "about" refers to a quality wherein the means to satisfy a specific need is met, e.g., the size may be largely but not wholly that which is specified but it meets the specific need of cartilage and/or bone repair at a site of cartilage and/or bone repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2.

In one embodiment, the term "void" refers to a space not occupied. In the instant invention, for example, in one embodiment, a void may be a space in a scaffold naturally not occupied. In one embodiment, a void may be a space not occupied at a site of repair. In one embodiment, a void may be a space not occupied within a scaffold of the current invention. In one embodiment, a void may be a volume of a pore or a pore region.

In one embodiment, coral is washed, bleached, frozen, dried, sterilized or a combination thereof. In some embodiments, the coral is processed as exemplified further hereinunder. In some embodiments, the coral, once processed into the scaffolds of this invention are seeded with a desired population of cells or populations of cells, prior to implantation within a site of cartilage and/or bone repair.

In one embodiment, this invention provides a process for the preparation of a multi-phasic scaffold for the repair of cartilage, said process comprising the steps of:

contacting only a portion of a solid form of aragonite or calcite with a calcium chelator and an acid to yield a solid form comprising enlarged voids in at least a portion of said solid form; and washing and drying said solid form under applied negative pressure.

In some embodiments, the calcium chelator is EDTA. In one embodiment, the chelator may comprise: ethylenediamine-N,N,N',N'-tetraacetic acid (EDTA), O,O'-bis(2-aminophenylethyleneglycol)ethylenediamine-N,N,N',N'-tetraacetic acid (BAPTA), N,N-bis(2-hydroxyethyl) glycine (Bicine), trans-1,2-diaminocyclohexane-ethylenediamine-N,N,N',N'-tetraacetic acid (CyDTA), 1,3-diamino-2-hydroxypropane-ethylenediamine-N,N,N'N'-tetraacetic acid (DPTA-OH), diethylenetriamine-N,N,N',N'',N''-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis (methylenephosphonic acid) (EDTPO), O,O'-bis(2-aminoethyl) ethyleneglycol tetraacetic acid (EGTA), N,N'-bis(2-hydroxybenzyl)ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N'-tetrakis(2-pyridylmethyl)ethylenediamine (TPEN), and triethylenetetramine-N,N,N',N'',N''-hexaacetic acid (TTHA), rhod-2, DMSA, FLUO 3, FURA 2, INDO 1, QUIN 2, or other chelators known in the art, or a combination thereof.

In some embodiments, the acid is formic acid. In some embodiments, the acid is a weak acid, such as picric acid, acetic acid, or others known to the skilled artisan. In some embodiments, the acid is a strong acid such as hydrochloric acid, nitric acid, sulfuric acid, or others, known to the skilled artisan. In some embodiments, the acid is a hydrogen halide, halogen oxoacid, such as: hypochloric acid, chloric acid, perchloric acid, periodic acid a fluorosulfuric acid, a nitric acid, a phosphoric acid, a fluoroantimonic acid, a fluoroboric acid, a hexafluorophosphoric acid, acetic acid, citric acid, gluconic acid, lactic acid, oxalic acid, tartaric acid or a chromic acid.

Without being bound by theory, the processes of this invention make use of calcium chelator, which acts as a slow decalcificator of the coralline material. The chelator, for example, EDTA, binds ionized calcium present on the outer layer of the mineral crystal, slowly reducing the size of the crystal. Addition of a chelator alone may in some embodiments, be sufficient to arrive at the scaffolds of this invention.

In accordance with this aspect, the coralline material is further contacted with an acid, for example, formic acid. Without being bound by theory, the addition of the acid results in faster dissolution of the coralline material, as compared to samples contacted with a chelator alone.

In some embodiments, the combined application of chelator and acid results in a controlled dissolution, providing for a homogenous pore size and volume.

In some embodiments, the choice of chelator, or acid, the concentration of each, or a combination thereof will provide for additional control of the enlarged voids within the thereby produced coralline-based scaffolds of this invention. It will be appreciated that the artisan will pick a weak or strong acid, at high or low concentration, and favor certain calcium chelators to arrive at a desired pore volume or average diameter for the voids enlarged in the scaffolds as herein described, produced by the methods of this invention and such choice is to be considered an embodied aspect of the processes of this invention. For example, and in some embodiments, the chelator concentration will range from about 0.1%-about 20% over a time course of about 5 minutes to about 24 hours, and in some embodiments, according to this aspect, the acid concentration will range from about 0.01% to about 10%, over a time course of about 0.1 minute to about 24 hours.

According to this aspect, and in some embodiments, the contacting is conducted for a duration and under conditions, which vary as a consequence of the desired final geometry of the scaffold.

In one embodiment of this invention, the term "portion" refers to a limited part of a whole. In one embodiment, the term "portion" with regard to the surface exposed as a consequence of the methods of this invention refers to a limited part of a whole exposed surface. For example, in one embodiment a portion of an exposed surface comprises less than 100% of the exposed surface. In one embodiment a portion of an exposed surface comprises less than 90% of the exposed surface. In one embodiment a portion of an exposed surface comprises less than 80% of the exposed surface. In one embodiment a portion of an exposed surface comprises less than 70% of the exposed surface. In one embodiment a portion of an exposed surface comprises less than 60% of the exposed surface. In one embodiment a portion of an exposed surface comprises less than 50% of the exposed surface. In one embodiment a portion of an exposed surface comprises less than 40% of the exposed surface. In one embodiment a portion of an exposed surface comprises less than 30% of the exposed surface. In one embodiment a portion of an exposed surface comprises less than 20% of the exposed surface. In one embodiment a portion of an exposed surface comprises less than 10% of the exposed surface. In one embodiment a portion of an exposed surface comprises less than 1% of the exposed surface.

In one embodiment of this invention, the term "surface" refers to an exterior or upper boundary of an object.

In one embodiment of this invention, the term "exposed" refers to being open to the surrounding environment such that contact may occur between a scaffold of this invention and the immersion media.

According to this aspect, and in other embodiments, the solid form produced by said process comprises at least two phases, which phases differ in their pore volume, or which phases comprise voids which differ in terms of the average diameter of said voids, or a combination thereof. In some embodiments, the method as herein described is one means by which the scaffolds as described hereinabove may be prepared.

In some embodiments, this invention provides a scaffold produced according to a process of this invention.

In some embodiments, the methods of this invention result in scaffolds produced comprising phases, which differ in terms of the average diameter of voids contained therein, or differ in terms of the pore volume within phases created in the scaffold thereby, or differ in terms of a combination thereof, which average diameter and/or pore volume are smaller or larger than the ranges as described herein. It is to be understood that such scaffolds, as created by the methods of this invention represent envisioned embodiments of this invention and part of this invention.

In one embodiment, a scaffold of this invention comprises a solid throughout a scaffold. One skilled in the art will recognize that solid scaffolding of this invention still comprises pore-like cavities and/or interstices.

In one embodiment, a scaffold of this invention comprises a hollow along a Cartesian coordinate axis of a scaffold. In one embodiment, the hollow is along a long axis of a scaffold of this invention. In one embodiment, the term "hollow" refers to a cavity within a scaffold of this invention. In one embodiment, the hollow comprises at least a single opening in the scaffold such that the cavity is exposed to the external environment. In one embodiment, the hollow provides additional exposed surface area for a scaffold of this invention.

In some embodiments, the scaffolds of this invention will comprise multiple hollows, which may be in any orientation, or in some embodiments, the scaffolds of this invention will comprise a network of hollows within scaffolds, or in some embodiments, multiple scaffolds are implanted into a repair site, wherein hollows of the scaffolds are aligned to form a network of hollows throughout the implanted scaffolds.

It will be appreciated by the skilled artisan that methods for selective creation of hollows or voids (which words may be used interchangeably throughout) within the scaffolds of this invention may be prepared by any means known to the skilled artisan, for example, in accordance with the methods as herein described, for example, by replacing immersion dipping of the portion of the scaffold with drip application of the immersion solution to selectively create voids within the scaffolds of this application.

The exposed surface area of a scaffold of this invention provides a location for mesenchymal stem cells, chondrocytes, osteoblasts, etc., attachment, growth, proliferation or differentiation, or a combination and a location for blood vessels formation. Therefore, the surface area of a scaffold of this invention ultimately provides a beneficial location for regeneration of cartilage and/or bone tissue. In one embodiment of this invention, a scaffold comprises a hollow, wherein the presence of the hollow increases the exposed surface area of a scaffold compared to an analogous scaffold without a hollow.

In one embodiment of this invention, the scaffold comprises a polymer coating.

The term "polymer coating" refers, in some embodiments, to the presence of a layer of polymeric material in association with at least a portion of the scaffolding material. In some embodiments, such coating may be over the entirety of the scaffold, and in some embodiments, such coating may penetrate to within the voids and/or pores and/or hollows of the scaffold. In some embodiments, such coating may be selectively applied to a particular region of the scaffold, such that it creates a separate phase on the scaffold, and in some embodiments, such polymer may be so applied that a thick polymer layer or phase is associated with a portion of a scaffold, thereby creating a separate polymer phase in association with the scaffolds as herein described. In some embodiments, biocompatible polymers are envisioned.

In one embodiment, the polymer coating strengthens the scaffold and in some embodiments, the polymer coating results in greater cellular attraction and attachment to the scaffolding, which in turn, inter alia, results in enhanced repair in terms of quantity, quality and timing of repair. In some embodiments, the polymer coating enhance cells proliferation and/or differentiation into cartilage and/or bone which in turn, inter alia, results in enhanced repair in terms of quantity, quality and timing of repair.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof.

In one embodiment, a polymer coating of this invention is discontinuous. In one embodiment, a region or a plurality of sub-regions of the coral of this invention comprise an absence of polymer coating, allowing direct contact between the coral and the environment.

In some embodiments, the scaffold incorporates a biocompatible polymer therewithin, which is associated with the aragonite or calcite component, via any physical or chemical association. In some embodiments, the polymer is a part of a hydrogel, which is incorporated in the scaffolds of this invention. In some embodiments, such hydrogel-containing scaffolds may thereafter be lyophilized or dessicated, and may thereafter be reconstituted.

In some embodiments of the scaffolds of this invention containing two separate phases, the biocompatible polymers are incorporated in the first phase alone or in the second phase alone.

Such polymer-containing scaffolds may be particularly suited for cartilage repair, regeneration or enhancement of formation thereof. In some embodiments, according to this aspect, for example, in the treatment of osteochondral defects, the coralline-based scaffolding is of a dimension suitable for incorporation within affected bone, and further comprises a polymer-containing phase, which phase, when inserted within the affected defect site, is proximal to affected cartilage. In another aspect and representing an embodiment of this invention, the scaffold comprises a polymer, which has permeated within the voids and pores of the scaffold, which scaffold is inserted within a site of cartilage repair and which polymer facilitates cartilage growth, regeneration or healing of the defect site.

Such polymer-containing scaffolds may be particularly suited for bone repair, regeneration or enhancement of formation thereof. In some embodiments, according to this aspect, for example, in the treatment of bone breakage or fragmentation, disease or defect, the coralline-based scaffolding is of a dimension suitable for incorporation within affected bone, and further comprises a polymer, which polymer has permeated within the voids and pores of the scaffold, which scaffold is inserted within the bone and which polymer facilitates bone growth, regeneration or healing of the defect site.

In one embodiment, a polymer coating of this invention comprises a natural polymer comprising, collagen, elastin, silk, hyaluronic acid, sodium hyaluronate, cross linked hyalronic acid, chitosan, cross linked chitosan, alginate, calcium alginate, cross linked calcium alginate and any combinations thereof.

In one embodiment, the polymer comprises synthetically modified natural polymers, and may include cellulose derivatives such as alkyl celluloses, hydroxyalkyl celluloses, cellulose ethers, cellulose esters and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly(ketal), poly(caprolactone), poly(acetal), poly($\alpha$-hydroxy-ester), poly($\alpha$-hydroxy-ester), poly(hydroxyl-alkanoate), poly(propylene-fumarate), poly (imino-carbonate), poly(ester), poly (ethers), poly(carbonates), poly(amide), poly(siloxane), poly (silane), poly(sulfide), poly(imides), poly(urea), poly(amide-enamine), poly(organic acid), poly(electrolytes), poly(p-dioxanone), poly(olefin), poloxamer, inorganic or organomatallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-($\epsilon$-caprolactone)]; poly[glycolide-co($\epsilon$-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, $\alpha$-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan ($\chi$, $\lambda$, $\mu$, $\kappa$), chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly($\beta$-hydroxybutyrate), poly (3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a coral of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio)propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thererof.

In one embodiment, the cross-linking agent is a heterobifunctional cross-linker, such as, for example, an amine-reactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl) butyric acid hydrazide), or a combination thereof.

In some embodiments, the cross-linking agent is a trifunctional cross-linkers, such as, for example, 4-azido-2-nitrophenylbiocytin-4-nitrophenyl ester, sulfosuccinimidyl-2[6-biotinamido]-2-(p-azidobenzamido)hexanoamido]ethyl-1, 3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a coral of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

It will be apparent to one skilled in the art that the physical and/or chemical properties of a polymer coating and components thereof may influence methods of use of this invention and kits thereof, for inducing or enhancing cartilage and/or bone repair.

In one embodiment, the polymer coating of this invention has a thickness of between 2.0 μm and 0.1 μm. In one embodiment, the polymer coating has a thickness of about 1.0 μm. In one embodiment, the polymer coating of this invention has a thickness of between 10 μm and 50 μm. In one embodiment, the polymer coating has a thickness of about 10-25, or about 15-30, or about 25-50 μm.

In some embodiments, the polymer coating is a thin coating, which is associated with the scaffolds of this invention nad has a thickness as indicated hereinabove.

In some embodiments, the polymer coating is applied throughout the scaffolds of this invention, such that, in some embodiments, the pores and voids within the scaffolds of the invention may be filled with polymers as herein described, and such polymer coatings may have a thickness of about 60-900 μm.

In some embodiments, the polymer coating is applied to a terminus or a portion of the coating forming an additional polymer phase on the scaffolds of the invention. According to this aspect, and in some embodiments, the polymer coating will have a thickness of between about 0.1-10 mm.

In some embodiments, multiple scaffolds comprising polymer coatings are implanted into a repair site, wherein the coating thickness of a first scaffold may vary as compared to a coating thickness of a second scaffold, implanted in the repair site. Variations in the coating thickness may reflect the range described herein.

In one embodiment, the thickness of the polymer coating influences physical characteristics of a scaffold of this invention. For example, the thickness of a polymer coating may influence elasticity, tensile strength, adhesiveness, or retentiveness, or any combination thereof of a scaffold of this invention. In one embodiment, a polymer coating increases the elasticity of a scaffold of this invention. In one embodiment, a polymer coating increases the tensile strength of a scaffold of this invention. In one embodiment, the adhesiveness of a polymer coating relates to adhesion of mesencymal stem cells, blood vessels, tissue at a site of cartilage repair, cartilage tissue, or bone tissue, or a combination thereof. In one embodiment, a polymer coating decreases the adhesiveness of a scaffold of this invention. In one embodiment, a polymer coating increases the adhesiveness of a scaffold of this invention. One skilled in the art will recognize that a polymer coating may increase adhesiveness for an item while decreasing adhesiveness for another item. For example, in one embodiment, the polymer coating increases adhesiveness for a mesenchymal stem cell and decreases adhesiveness of an infective agent. In one embodiment, the retentiveness of a polymer coating relates to retention of a cell population. In one embodiment, the cell population retained within a polymer coating is a mesenchymal stem cell population, chondrocyte population osteoblast population, etc. In one embodiment, the retentiveness of a polymer coating relates to retention of effector compounds.

In one embodiment, the thickness of the polymer coating influences proliferation and/or differentiation of mesenchymal stem cells applied to the scaffolds of this invention, or influences the activation or migration of cells associated with cartilage and/or bone formation or repair to the scaffolds of this invention, or a combination thereof.

In one embodiment of this invention, the cells as used in accordance with the scaffolds, methods of use or kits of this invention, are engineered to express a desired product.

In one embodiment, a polymer coating of this invention comprises an effector compound. In one embodiment, the effector compound is applied directly to a polymer coating of the scaffold of this invention. In one embodiment, the effector compound comprises a component of a kit of this invention for use for incorporation into a scaffold of this invention as herein described. In one embodiment, the effector compound is applied directly to a polymer coating of this invention, without being dispersed in any solvent.

In one embodiment of this invention, the polymer coating comprises an effector compound comprising a cytokine, a bone morphogenetic protein (BMP), growth factors, a chelator, a cell population, a therapeutic compound, or an antibiotic, or any combination thereof.

In one embodiment, effector compounds for use in a scaffold and/or a kit of this invention and/or a method of this invention may comprise, inter-alia, a cytokine, a bone morphogenetic protein (BMP), growth factor, a chelator, a cell population, a therapeutic compound, an anti-inflammatory compound, a pro-angiogenic compound or an antibiotic, or any combination thereof.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be incorporated into a polymer coat, or a scaffold of this invention, or a combination thereof.

In one embodiment, transfected, transduced or transformed cells, may be incorporated into a polymer coating, or a scaffold of this invention In one embodiment, a cell population of this invention comprises mesenchymal stem cells. In one embodiment, the mesenchymal stem cells are transformed. In one embodiment, a cell population comprises cells beneficial in cartilage and/or bone formation and/or repair, such as chondroblasts or chondrocytes; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. the precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the a family, transforming growth factors of the β family, gastrins, secretins, cholecystokinins, somatostatins, serotonins, substance P, transcription factors or combinations thereof.

In one embodiment, the effector compound comprises, an anti-helminth, an antihistamine, an immunomodulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the scaffolds, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the scaffold and/or kits of this invention, or whose use thereof, is desired. In one embodiment, the agent is incorporated directly within a scaffold, and/or kit of this invention. In another embodiment, the agent is incorporated within a scaffold and/or kit of this invention, either by physical interaction with a polymer coating, a coral, or coral particles of this invention, and/or a kit of this invention, or association thereto.

In one embodiment, compounds for use in a scaffold and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the scaffolds and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The scaffolds and/or kits of this invention and/or methods of use of this invention may comprise nucleic acids, in one embodiment, or in another embodiment, the scaffolds and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, the scaffold of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the scaffold of this invention incorporates any cell which may participate in cartilage and/or bone formation or repair. In some embodiments, such cells represent autografts, in that cells are cultured ex-vivo to seed the cells on the scaffolds of the invention, and such seeded scaffolds are implanted into the subject.

In some embodiments, such cells may represent allografts or xenografts, which may be incorporated within the scaffolds of this invention and implanted within a site of repair.

In one embodiment, a coral of this invention comprises a cell population from in vitro culture of the coral for a time period sufficient to seed the cells in the coral. In one embodiment, the cell population is a mesenchymal stem cell population, chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In one embodiment, the mesenchymal stem cells; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof seeded in vitro are transformed. In one embodiment, the cell population comprises a cell population beneficial for cartilage repair. In one embodiment, the culture comprises a chelator. In one embodiment of this invention, the chelator in a culture comprises a calcium chelator.

In one embodiment, a method of this invention induces or enhances cartilage and/or bone formation and/or repair, wherein the method comprises implanting in a subject, a scaffold of this invention within a site of cartilage and/or bone formation and/or repair, wherein a region of the scaffold penetrates through a bone, resulting in the region inserting within a bone marrow void, proximal to the site of cartilage and/or bone formation and/or repair.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a full or partial thickness articular cartilage defect. In one embodiment, restoring cartilage results in complete or partial regeneration of cartilage tissue at a site of cartilage repair. In one embodiment, cartilage repair may result in restoration/repair of missing or defective bone tissue, wherein repair of a cartilage defect necessitates removal of bone tissue at a site of cartilage repair. In one embodiment, restoring cartilage results in regeneration of osteochondral defect. In one embodiment, cartilage repair comprises restoring cartilage defects of joints (e.g. knee, elbow, hip, shoulder joints), of ears, of a nose, or of a wind pipe.

In one embodiment, the phrase "bone repair" refers to restoring a bone defect to a more healthful state. In one embodiment, restoring bone results in regeneration of bone tissue. In one embodiment, restoring bone results in the filling in of any fracture or void within a bone tissue. In one embodiment, restoring bone results in complete or partial regeneration of bone tissue at a site of bone repair. In one embodiment, bone repair may result in restoration/repair of missing or defective bone tissue. In one embodiment, bone repair comprises restoring bone defects of any bone, as needed.

In some embodiments, the phrase "bone repair" refers to the treatment of a subject with osteoporosis, Paget's disease, fibrous dysplasias, or osteodystrophies. In another embodiment, the subject has bone and/or cartilage infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

The scaffolds, kits and methods of the invention may also be used to enhance bone and/or cartilage formation in conditions where a bone and/or cartilage deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment, fractures meant to be treated using the methods of the present invention are nonunion fractures.

In one embodiment, the scaffolds, kits and methods of the invention may also be used to augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the scaffolds, kits and methods of the invention may also be used in a method to accelerate the repair of fractured long bones; treat of delayed union or non-unions of long bone fractures or pseudoarthrosis of spine fusions; induce new bone formation in avascular necrosis of the hip or knee, or a combination thereof.

In one embodiment, a method of this invention comprises inducing and enhancing cartilage and/or bone repair wherein implanting a scaffold of this invention within a site of cartilage and/or bone repair influences and improves cartilage and/or bone repair.

In one embodiment, a method of this invention induces or enhances cartilage and/or bone repair, wherein the scaffold attracts a population of cells to the scaffold, thereby influencing or improving cartilage and/or bone repair.

The 3-D architecture and chemical composition of a scaffold of this invention are of great importance for specifically positioning and confining a scaffold within a site of cartilage and/or bone repair; for cellular recognition, adhesion, proliferation and differentiation of cell populations which induce or enhance cartilage and/or bone repair or a combination thereof In one embodiment, a scaffold of this invention utilized in a method of this invention comprises a seeded cell population prior to being implanted in a subject. In one embodiment, a method of this invention induces or enhances cartilage and/or bone repair, wherein implanting in a subject a scaffold of this invention promotes adhesion, proliferation or differentiation, or a combination thereof of transformed mesenchymal stem cells. In one embodiment, a method of this invention induces or enhances cartilage and/or bone repair, wherein implanting in a subject a scaffold of this invention promotes blood vessel formation.

In one embodiment, a scaffold utilized in methods of this invention comprises at least a region which specifically positions and confines the coral scaffold at an optimal depth and angle within a site of cartilage and/or bone repair, such that implanting the scaffold in a subject induces or enhances cartilage and/or bone repair. In one embodiment, a scaffold utilized in methods of this invention comprises at least a region which specifically positions and confines the coral at an optimal depth and angle within a site of cartilage and/or bone repair, such that implanting the scaffold maximizes the contact area between a scaffold of this invention and a site of cartilage and/or bone repair.

In one embodiment, a scaffold utilized in a method of the present invention may be used to adsorb or bind, and deliver, other therapeutically active substances which assist in the cartilage and/or bone repair or regeneration process, or which have other desired therapeutic activity. Such substances include, by way of example, known synthetic or semisynthetic antibiotics which may be introduced into the pore cavities of the shaped product or structure, or a growth factor such as transforming growth factor or one of the bone morphogenic proteins which can be used to assist or promote bone growth.

In any of the embodiments herein, scaffolds for use in the methods of the present invention may further comprise, or be implanted with, other compounds such as, for example, antioxidants, growth factors, cytokines, antibiotics, antiinflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In one embodiment, a method of this invention comprises implanting a scaffold of this invention in a subject afflicted with a cartilage and/or bone defect or disorder or disease.

In one embodiment, the term "implanting" refers to inserting and fixing a scaffold of this invention within a living site in a subject, the site comprising a site of cartilage and/or bone repair. In one embodiment, a method of this invention implants a scaffold such a region of the scaffold now has access to mesenchymal stem cells, nutrients, blood vessels, or effector compounds, or any combination thereof, In one embodiment, a method of this invention comprises implanting in a subject a scaffold of this invention, wherein the method results in removing a region of cartilage and/or bone and/or other tissue so that a region of the scaffold penetrates through the cartilage and/or bone and/or other tissue, and in sonic embodiments, reaches a bone marrow void.

A clinician skilled in the art will recognize that methods of this invention, which entail implanting a scaffold within a site of cartilage and/or bone repair, may require preparation of a site of cartilage and/or bone repair. These preparations may occur prior to implantation of a scaffold or simultaneously with implantation. For example, cartilage and/or bone tissue and/or other tissues proximal to a site of cartilage and/or bone repair may initially be drilled through to create a channel of dimensions appropriate for a scaffold used in the methods of this invention. Then the scaffold is implanted within the site so that a region of the scaffold penetrates the drilled cartilage and/or bone tissues. Alternatively, the scaffold may be attached to a tool of this invention capable of penetrating through cartilage and/or bone or other tissues, or a combination thereof. In this case, as the tool penetrates through the cartilage and/or bone tissue, the attached scaffold is simultaneously implanted.

In some embodiments, following implantation of the scaffold within a repair site, or several scaffolds within the repair site, the scaffold is processed to optimize incorporation and optimal cartilage and/or bone repair. In some embodiments, such processing may comprise cutting, sanding or otherwise smoothing the surface of the scaffold or scaffolds, for optimal repair.

In one embodiment, methods of this invention comprise implanting a scaffold in a human subject.

In one embodiment, methods of this invention may involve placement of a scaffold on a surface at site of cartilage and/or bone repair. In one embodiment, methods of this invention may involve components of a tissue milieu at a site of coral repair migrating to an exposed surface of a coral and contact between the coral of this invention would be made thus with the environment.

In one embodiment, methods of this invention may involve implanting a scaffold so that raised exposed surfaces of the scaffold forcefully contact the tissue at or adjacent to a site of cartilage and/or bone repair. In this way, the exposed surface of coral now proximal to a site of cartilage and/or bone repair is proximal to an environment comprising cartilage tissue, bone tissue, bone marrow tissue, mesenchymal stem cells, nutrients, blood vessels or other effector compounds, or a combination thereof, which may be beneficial to cartilage and/or bone repair.

In one embodiment of this invention, the phrases "long axis of the scaffold" and longitudinal axis of the scaffold" are used interchangeably and refer to a line extending parallel to the scaffold lengthwise. The term "lengthwise" refers the direction of the length of a scaffold. It may be that an original geometric shape has been cut to produce a horizontal section of the original scaffold. In such instances lengthwise should be viewed as being the original direction of length along a scaffold.

It will be apparent to one skilled in the art that the physical and/or chemical properties of a scaffold of this invention and components thereof may influence methods of use of this invention and kits thereof, for inducing or enhancing cartilage and/or bone repair.

In one embodiment, methods of this invention for inducing or enhancing cartilage and/or bone repair utilize the 3-D geometry of a scaffold of this invention to provide for specifically positioning and confining the scaffold within a site of cartilage and/or bone repair.

In one embodiment, the term "proximal" refers to something being situated close to a particular locale. In one embodiment, a scaffold of this invention is forcibly held in position within a site of cartilage and/or bone repair by a raised region of the scaffold contacting tissue situated at or proximal to a site of cartilage and/or bone repair.

One skilled in the art will recognize that the shape of a site of cartilage and/or bone repair and the shape of a 3-D scaffold of this invention provide many different combinations for stably positioning a scaffold within a site of cartilage and/or bone repair. In one embodiment, a scaffold of this invention is shaped prior to use in methods of this invention for cartilage and/or bone repair. In one embodiment, a scaffold of this invention is shaped concurrent to use in methods of this invention for cartilage and/or bone repair. By shaping a scaffold concurrent with use of the scaffold in methods of this invention, the dimensions of the scaffold may be precisely selected for specific positioning of the scaffold within a site of repair.

In one embodiment, methods of this invention comprise implanting a scaffold in a non-human mammalian and non-mammalian subject. In one embodiment, methods of this invention comprise implanting a scaffold in a horse, a race horse, a cow, a steer, a pig, a rabbit, a goat, a sheep, a farm animal, a pet, a dog, a cat, a monkey, an ape, a bird and an ayes In one embodiment, methods of this invention are utilized for induced or enhanced repair of a cartilage and/or bone defect or disorder or disease. In one embodiment, the cartilage defect results from a trauma, a tear, a sports injury, a full thickness articular cartilage defect, a joint defect, or a repetitive stresses injury (e.g., osteochondral fracture, secondary damage due to cruciate ligament injury). In one embodiment, the cartilage disorder comprises a disease of the cartilage. In one embodiment, methods of this invention induce or enhance cartilage repair in osteoarthritis, rheumatoid arthritis, aseptic necrosis, osteochondritis dissecans, articular cartilage injuries, chondromalacia patella, chondrosarcoma, chondrosarcoma-head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, a cartilage and/or bone defect or disorder or disease repaired by the methods of this invention utilizing a scaffold and/or at least a tool of this invention, comprises a joint of a subject (e.g. a knee, elbow, ankle, shoulder, or hip joint), a rotator cup, an ear, a nose, a windpipe, a pelvis, a spine, a rib, a jaw, a skull or any other site of cartilage and/or bone defect or disorder or disease found within the subject.

In one embodiment, the 3-D shape and chemical composition of a scaffold of this invention, used in the methods and/or kits of this invention will be determined by skilled clinicians, based on factors such as exact nature of the condition being treated, the severity of the condition, the age and general physical condition of the subject, body weight, and response of the individual subject, etc.

In one embodiment, the specific positioning of a scaffold of this invention during methods of this invention will be determined by skilled clinicians, based on factors such as exact nature of the condition being treated, the severity of the condition, the age and general physical condition of the subject, body weight, and response of the individual subject, etc.

In one embodiment, methods of this invention are evaluated by examining the site of cartilage and/or bone tissue repair, wherein assessment is by histology, histochemistry, palpation, biopsy, endoscopy, arthroscopy, or imaging techniques comprising X-ray photographs, computerized X-ray densitometry, computerized fluorescence densitometry, CT, MRI or another method known in the art, or any combination thereof.

In one embodiment, this invention provides an instrument to aid in cartilage and/or bone repair comprising a tool to guide a scaffold of this invention to an optimal angle at a site of cartilage and/or bone repair, a tool to guide a scaffold of this invention to an optimal angle at a site of cartilage and/or bone repair, a tool to deliver a scaffold of this invention to a site of cartilage and/or bone repair, a tool to insert a scaffold of this invention at a site of cartilage and/or bone repair so that the scaffold penetrates through a cartilage and/or bone, and inserts within a bone marrow void, proximal to said site of cartilage and/or bone repair, a tool to release a scaffold of this invention at a site of cartilage and/or bone repair, or a tool able to provide a combination thereof, whereby the tool may be separated from the scaffold following placement of the scaffold within a site of cartilage and/or bone repair.

In one embodiment, the instrument of this invention comprises at least a single tool.

In one embodiment, methods of this invention utilize an instrument of this invention, wherein implanting a scaffold of this invention comprises specifically positioning and confining the coral at an optimal depth and angle within a site of cartilage and/or bone repair.

In some embodiments, such tools may comprise a tool for insertion of a scaffold into a repair site, which tool is specifically constructed to hold the scaffold and optimally position it within the site. In some embodiments, multiple tools for different sized or shaped scaffolds may be incorporated within kits of the invention, to accommodate the implantation of varied scaffolds within a site or sites of cartilage and/or bone repair. In some embodiments, the kits of this invention will comprise a tool to process the scaffold following insertion within the site of repair, to affect a smooth optimal surface for optimal cartilage and/or bone repair. In some embodiments, the kits of this invention may further comprise a tool for creating a void between the repair site and a source of mesenchymal stem cells. In some embodiments, the kits may comprise a piece, which inserts within a common tool to effect such a void, for example, a drill bit is included in the kits of this invention of a size and depth to easily and appropriately drill through nearby bone in order that the scaffolding may be inserted in a site of cartilage and/or bone repair, where at least a portion of the scaffold, or contiguous scaffolds insert within a site of cartilage and/or bone repair and reach underlying bone marrow, to serve as a source for migrating mesenchymal stem cells to effect cartilage and/or bone repair.

One skilled in the art will recognize that the path created by drilling through tissue to reach a bone marrow void is such that it allows for a scaffold of this invention to reach the bone marrow void and be stably implanted at this site. The scaffold must be sufficiently secured within a site of cartilage and/or bone repair so that it does not get dislodged as a joint articulates. A clinician skilled in the art will also recognize that the extent of a drilled path is such that a scaffold is securely held but the path is not so extensive to incur increased damage to surrounding tissue.

Preparation of a site of cartilage and/or bone repair may also involve removing damaged cartilage or bone tissue, or a combination thereof. Therefore, in one embodiment, a tool of this invention drills a path such that damaged tissue at the site of repair or proximal to a site of repair is removed.

A tool of this invention may prepare the pathway a scaffold will follow, guide the scaffold being implanted, and implant the scaffold concurrently. By concurrently preparing the site and implanting the scaffold, the time of invasive or minimal-invasive surgery a subject is subjected to may be shortened.

In one embodiment, a region of the scaffold separates from the tool following placement of the scaffold within the site of cartilage repair. In one embodiment, the region separates from the tool, wherein separation of the tool from the scaffold comprises UV light-activated separation, LASER-activated separation, torsion-dependent separation or chemically-activated separation or a combination thereof. In one embodiment, separation of the tool from the scaffold leaves behind the scaffold specifically positioned within a site of repair. The mechanism for separation should also not cause additional trauma to a site of repair.

In one embodiment, separation of the tool from the scaffold results in the scaffold being specifically positioned and confined at an optimal depth and angle within a site of cartilage and/or bone repair. In one embodiment, separation of the tool from the scaffold results in the scaffold being implanted in a subject within a site of cartilage and/or bone repair, wherein a region of the scaffold penetrates through cartilage and/or bone, results in the region inserting within a bone marrow void, proximal to the site of cartilage and/or bone repair.

In one embodiment, this invention provides a kit for repair of tissue comprising the scaffold of this invention, at least a tool of this invention, and directions for utilizing the scaffold in tissue repair.

One skilled in the art will recognize that choice of a kit by a skilled clinician would be dependent upon factors such as exact nature of the condition being treated, the severity of the condition, the age and general physical condition of the subject, body weight, and response of the individual subject.

Thus, in one embodiment, the scaffold comprised in a kit of this invention comprises different sizes, shapes or chemical compositions, or a combination thereof. In one embodiment, this invention provides a kit for cartilage and/or bone repair comprising a scaffold of this invention, at least a tool of this invention, and directions for utilizing the scaffold in cartilage repair.

Thus, the invention provides embodiments that include, inter alia, Embodiments 1-36 below:

Embodiment 1: A scaffold for tissue repair, said scaffold consisting essentially of two phases wherein:
  a first phase of said two phases comprises solid coral or biolattice comprising a biocompatible polymer and said first phase further comprises a series of hollows along a longitudinal axis in said first phase, wherein said biocompatibie polymer is substantially located within said series of hollows; and
  a second phase of said two phases comprises a solid coral or biolattice;

Embodiment 2: The scaffold of embodiment 1, wherein said biocompatible polymer is hyaluronic acid, sodium hyaluronate of chitosan, or a combination thereof;

Embodiment 3: The scaffold of embodiment 1, wherein said coral is from the *Porites species, Millepora species*, or *Acropora species*; Embodiment 4: The scaffold of embodiment 3, wherein said coral is *Porites Lutea*;

- Embodiment 5: The scaffold of embodiment 3, wherein said coral is *Millepora dichotoma*;

Embodiment 6: The scaffold of embodiment 3, wherein said coral is *Acropora grandis*;

Embodiment 7: The scaffold of embodiment 6, wherein said biocompatible polymer farther comprises an anti-inflammatory compound, an anti-infective compound, a growth factor, a chelator, an antibiotic, a cell population, a pro-angiogenic factor or a combination thereof;

Embodiment 8: The scaffold of embodiment 1, wherein said first phase is inserted into a region which is proximal to cartilage and said second phase is inserted into a region which is proximal to subchondral bone;

Embodiment 9: A scaffold for the repair, regeneration or enhancement of formation of cartilage, bone, or a combination thereof, which scaffold consists of a solid form of aragonite or calcite and further comprises:
  at least a first phase, comprising voids having an average diameter ranging from about 60-160 μm; and
  at least a second phase, comprising voids having an average diameter ranging from about 170-850 μm;

Embodiment 10: The scaffold of embodiment 9, further comprising a third phase, comprising voids having an average diameter ranging from about about 170-300 μm and said second phase comprises voids having an average diameter ranging from about 350-850 μm and said third phase is positioned between said first and second phase;

Embodiment 11: A scaffold for the repair, regeneration or enhancement of formation of cartilage, bone, or a combination thereof, which scaffold consists of a solid form of aragonite or calcite and further comprises:
  at least a first phase, comprising pores having a pore volume ranging from about 35-55%; and
  at least a second phase, comprising pores having a pore volume ranging from about 56-95%;

Embodiment 12: The scaffold of embodiment 11, further comprising a third phase, pores having a pore volume ranging from about 56-80%, wherein said second phase comprises voids having an average pore volume ranging from about 81-95% and said third phase is positioned between said first and second phase;

Embodiment 13: The scaffold of embodiments 9-12, wherein said solid form is isolated from a *Porites species*, a *Millepora species* or an *Acropora species*;

Embodiment 14: The scaffold of embodiment 13, wherein said solid form is isolated from *Porites Lutea*;

Embodiment 15: The scaffold of embodiment 13, wherein said solid form is isolated from *Acropora grandis*;

Embodiment 16: The scaffold of embodiments 1-4, wherein said scaffold is of a shape which accommodates a site of repair;

Embodiment 17: The scaffold of embodiments 9-12, wherein said scaffold approximates the form of a cylinder, cone, screw, rectangular bar, plate, disc, pyramid, granule, ball or cube;

Embodiment 18: The scaffold of embodiments 9-12, wherein said scaffold further comprises a hollow or hollows along a Cartesian coordinate axis of said scaffold in at least said first phase or at least said second phase;

Embodiment 19: The scaffold of embodiments 9-12, wherein said scaffold comprises a biocompatible polymer;

Embodiment 20: The scaffold of embodiment 19, wherein said biocompatible polymer is incorporated in said first phase alone or said second phase alone; Embodiment 21: The scaffold of embodiment 19, wherein said biocompatible polymer comprises a natural polymer comprising a glycosaminoglycan;

Embodiment 22: The scaffold of embodiment 19, wherein said glycosaminoglycan is hyaluronic acid;

Embodiment 23: The scaffold of embodiments 9-12, wherein said scaffold further comprises a cytokine, a bone morphogenetic protein (BMP), a chelator, a therapeutic compound, or an antibiotic, or any combination thereof;

Embodiment 24: The scaffold of embodiment 23, wherein said therapeutic compound comprises an antiinflammatory compound, an anti-infective compound, a growth factor, a pro-angiogenic factors or a combination thereof;

Embodiment 25: The scaffold of embodiments 9-12, wherein said scaffold is seeded with a cell population, which population comprises mesenchymal stem cells, osteoblasts, osteocytes, osteoclasts, chondroblasts, chondrocytes, fibroblasts, or a combination thereof;

Embodiment 26: The scaffold of embodiments 9-12, wherein said scaffold is cylindrical in shape and has a diameter of about 5-15 mm, and a height of about 5-25 mm;

Embodiment 27: A method of inducing or enhancing repair, regeneration or enhancement of formation of cartilage, bone or a combination thereof, said method comprising implanting in a subject, a scaffold of embodiment 1 or embodiments 9-12 within a site in need of repair, regeneration or enhancement of formation of cartilage, bone or a combination thereof;

Embodiment 28: The method of embodiment 27, wherein said method comprises exposing said site of cartilage repair, and optionally exposing bone tissue located proximally to the site of cartilage repair in said subject prior to implanting said scaffold;

Embodiment 29: The method of embodiment 28, further comprising the step of affixing at least a portion of said scaffold within bone located proximally to said site of cartilage repair;

Embodiment 30: The method of embodiment 29, wherein said method promotes adhesion, proliferation or differentiation, or a combination thereof, of a cell population to said scaffold;

Embodiment 31: The method of embodiment 29, further comprising seeding said scaffold with mesenchymal stem cells prior to said implanting;

Embodiment 32: The method of embodiment 29, wherein said subject is afflicted with a cartilage and/or bone defect or disorder or disease;

Embodiment 33: The method of embodiment 29, wherein said subject is a human subject;

Embodiment 34: The method of embodiment 29, wherein said subject is an animal subject;

Embodiment 35: The method of embodiment 29, wherein said cartilage defect or disorder comprises a full or partial thickness articular cartilage defect; osteochondral defect; osteoarthritis, a joint defect or a defect resulting from trauma, sports, or repetitive stress; and Embodiment 36: The method of embodiment 29, wherein said scaffold is positioned such that said at least a second porous phase is implanted within or proximally to cartilage tissue and said at least a first porous phase is implanted within or proximally to bone tissue.

It will be apparent to those skilled in the art that various modifications and variations can be made in the scaffolds, kits, process and methods of the present invention without departing from the spirit or scope of the invention.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Applications of Coralline-Based Scaffolding of this Invention

Coralline-based scaffolding of this invention may be inserted into cartilage, bone or a combination thereof, in a subject in need thereof.

In some embodiments, such placement will include drilling in the area to expose the site in which implantation is desired, and tight fitting of the scaffold within the defect/site.

For implantation for cartilage repair, regeneration, etc., scaffolds are implanted in the desired cartilage site, and within proximally located bone, so that, in this way, the coral scaffold is grafted through two types of tissue, cartilage and bone. FIG. 1 schematically depicts orientation of a cartoon of a scaffold of this invention within a site of cartilage/bone repair.

Scaffolds may be prepared according to any embodiment as described herein, as will be appreciated by the skilled artisan.

The scaffolds are envisioned for use in veterinary applications, as well as in the treatment of human subjects. It is to be understood that animal studies may be undertaken to determine optimum configurations and implantation parameters and procedures.

For example, animal studies may include implantation of a scaffold as described herein within an animal subject and scaffolds are examined and observed over an extended time period, post surgery. The untreated knee of each animal is used as a control for comparisons following such surgeries. At appropriate intervals, animals are sacrificed and histology performed. Appropriate time periods for examining the site of cartilage repair are 2.5, 4, 9, 12, 26, 52 weeks post surgery. At this time, the articular surfaces are photographed and tissue is removed from the site of repair and prepared for histological observations. Specifically, a block consisting of the grafted area and the surrounding tissue is removed using a fine saw. The material is further processed for routine histology, which includes slow decalcification.

Example 2

Restoration of an Osteochondral Defect

Restoration of an osteochondral defect was performed in mature goats using rounded implants which were 6 mm in diameter and 8 mm in length. A 5.5×8 mm core of cartilage and bone tissue was drilled out of the medial femoral condyle of each goat (FIG. 2A) and the implant pressed fit into the site of cartilage and bone repair (FIGS. 2B and 2C).

Some animals harvested at 2.5 weeks post surgery exhibited signs that the implant was well incorporated into the native tissue and cartilage tissue was developed proximal to implant, moreover signs of vascularisation were seen (FIG. 2C).

Figure 4B:
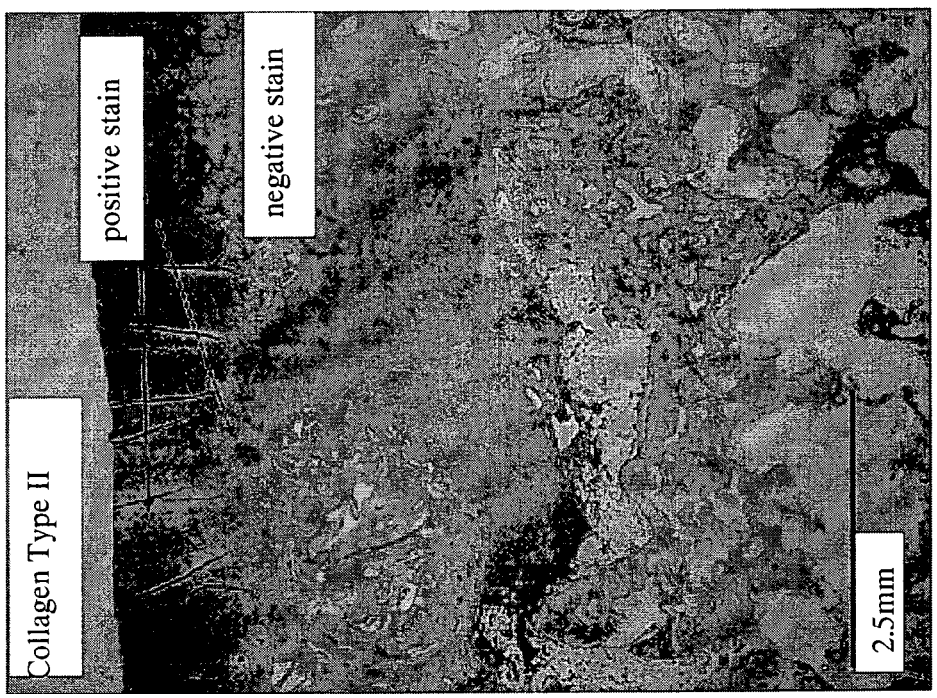
FIG. 4B shows a comparable section stained for detection of Collagen type II.
Figure 4A:
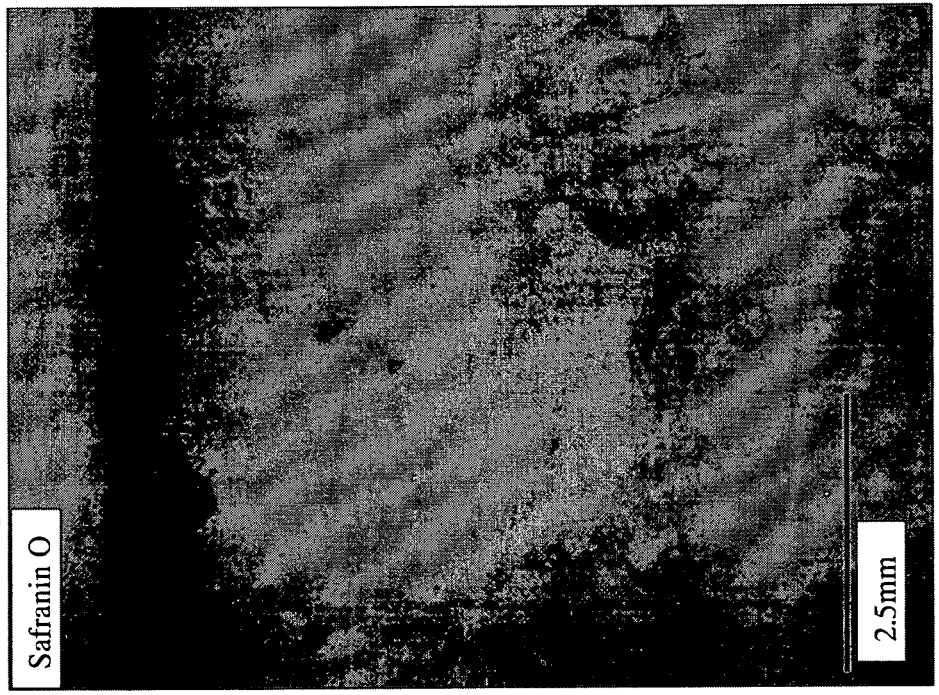
FIG. 4A presents a low magnification (2×) of the tissue 9 weeks after implantation in a medial femoral condyle of a goat; D=5 stained with Safranin O.

A group of animals were sacrificed and tissue was harvested from the implant site 9 weeks post surgery. H&E and Masson Trichrome histological evaluation of the tissue (FIGS. 3A and 3B, respectively) showed that area of the implant was replaced by newly formed cartilage and woven bone and the cartilage was smooth and almost completely regenerated. Safranin O staining and probing for Collagen type II expression revealed the existence of a homogeneous red band of cartilage covering normal bone (FIG. 4A), and collagen type II deposition along the band of cartilage (FIG. 4B). The regenerated cartilage was virtually indistinguishable from the adjacent normal cartilage. The repair surface was smooth with no evidence of fibrillation. Moreover, there was evidence of complete closing of the defect at the level of the articular cartilage and evidence of transformation of mesenchymal cells to chondrocytes and osteoblasts with formation and remodeling (by osteoclasts) of new subchondral bone. FIG. 11A and FIG. 11B show an H & E stain of similar sections showing regenerated cartilage.

Example 3

Preparation of a Multiphasic Solid Aragonite Scaffold

To create a multi-phasic scaffold varying in terms of the pore volume (porosity) of each phase, and/or varying in terms of the diameter of the voids present in each phase, plugs of 5.2 mm in diameter and 7.5 mm in length were positioned within a silicon holder whereby only the top 1 mm of the plug was exposed, and the holder with the plug was placed in an inverted position, and immersed into the reaction mixture, such that only the top 1 mm of the plug was in direct contact with the mixture.

The plug was first immersed in a 5% disodium salt solution for two hours at room temperature, followed by addition of a 99% formic acid solution to yield a final concentration of 0.5%, where the plugs were immersed again in the solution for an additional 20 minutes. The mixture was discharged and the plugs were washed in distilled water overnight, under conditions of approximately 0.2-0.00001 Bar pressure via the application of a vacuum following placement of the plug in a sealed container and applying the vacuum to the chamber. Plugs were vacuum dried overnight at room temperature.

Figure 6A:
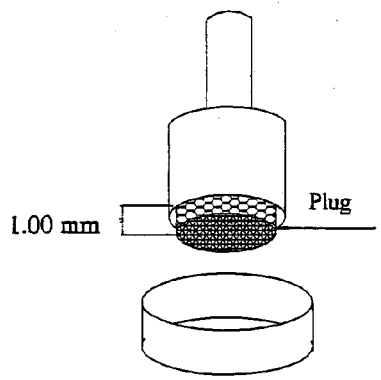
FIG. 6 depicts the preparation and use of an embodiment of a multi-gradient scaffold of the invention. An embodiment of the positioning of the plug within the sieve for immersion is shown in FIG. 6A.
FIGS. 6B and 6C depict light microscopy images of the top portion (panel B) cut from the plug (panel C) and visualized at higher magnification where the size of the voids can be ascertained.
FIG. 6D schematically depicts a multiphasic scaffold embodiment of this invention.

FIG. 6A depicts an embodiment of a holder exposing a portion of a plug for immersion as herein described.

Table 1 depicts the results of immersing 15 plugs isolated from different regions of the same piece of coral (*Porites Lutea*) processed as described in this example. A diamond saw was used to remove slices from individual phases and the slices were processed for light microscopy analysis and an optical bifocal microscope was used to image the scaffold; and images were captured and void diameters were assessed for size by standard methodology.

30 voids were identified in three different implants within the region of the plug immersed within the reaction mixture, 41 voids were identified in four different implants within the region located proximally to the immersion region and 46 voids were identified in four different implants within the region located distally to the immersion region, and the diameter of each void was determined. The result of these determinations is presented in Table 3 hereinbelow:

TABLE 1

|  | Immersed region of the implant | Proximal region | Distal region |
| --- | --- | --- | --- |
| Median | 700 | 200 | 110 |
| Std. Dev. | 50.2 | 69.8 | 39.9 |

Figure 6B:
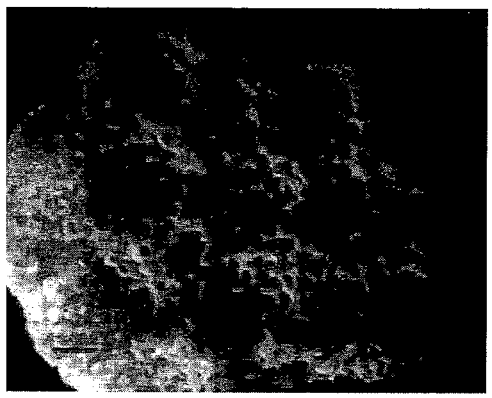
Figure 6C:
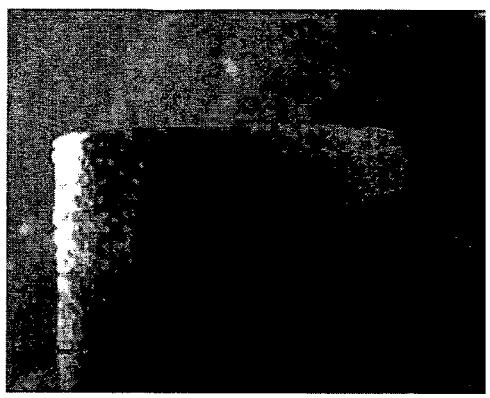
Figure 6D:
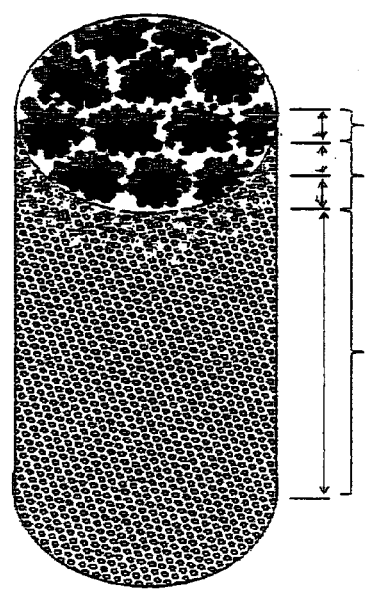
Figure 8A:
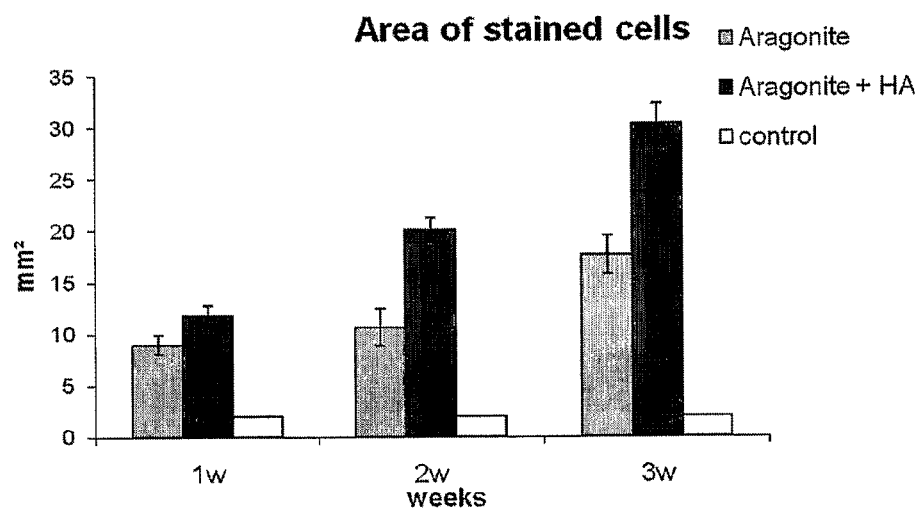
FIG. 8 shows the stained cell area (FIG. 8A) and intensity (FIG. 8B) of Safranin O/Fast Green staining of MSC cultured on Aragonite scaffold, Aragonite+hyaluronic acid and without any scaffold over time.
Figure 8B:
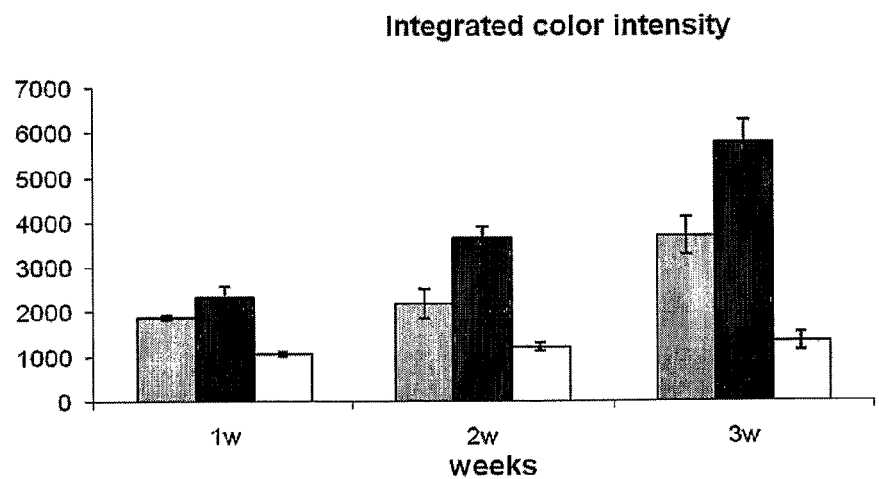

FIGS. 6B and 6C depict light microscopy images of the top portion (panel B) cut from the plug (panel C) and visualized at higher magnification where the size of the voids can be ascertained.

In terms of pore volume (porosity), the immersed portion exhibited from about 85-90% of the plug being porous, the proximal region thereto (having a length of about 0.5-1 mm along a longitudinal axis, located proximally to the immersed region) exhibiting about 65-75% porosity, while the distal region exhibited about 45-50% porosity.

Porosity was derived, as described (Karageorgiou V, Kaplan D. (2005) " Porosity of 3D biomaterial scaffolds and osteogenesis" Biomaterials.; 26(27):5474-91)

The porosity level can be controlled by parameters such as the type and concentration of the chelator utilized, the type and concentration of the acid utilized, temperature at which the method is conducted and time of reaction, while the size of the entire enlarged porous phase can be controlled by the length of the plug which is placed in direct contact with the reaction mixture.

Controlling of the porosity and the size of the different phases will allow for the design of implants for different purposes exhibiting different strengths, physical and structural characteristics which have the potential to mimic different native bones and cartilage structures. This control will provide a higher fitness of the implant to the exact desired location of implantation as is required from each specific cartilage/bone or only bone defect.

Example 4

Scaffolds of Aragonite Impregnated with Hyaluronic Acid are more Chondrogenic than Aragonite-Based Scaffolds In Vitro In order to evaluate the chondrogenic potential of the chondral phase of an implant, aragonite-based scaffolds were compared to aragonite impregnated with hyaluronic acid scaffolds. In vitro assays were conducted using the murine mesenchymal stem cells (MSCs) ATCC/CRL-12424 and their differentiation toward a chordrogenic lineage was assessed. 5000 MSCs were seeded onto 1 mg of small particles (~1 mm in size) of coralline-based (sp. *Porites Lutea*) aragonite with or without hyaluronic acid (NaHA 1%). A third group without any implants served as control. The methods of the scaffold preparation were described herein. The hyaluronic acid (HA) used was an injectable gel of 1% sodium hyaluronate marketed as Arthrease, manufactured by Bio-Technology General (Israel) LTD. Lot:RDO131B.

Each particle was individually cultured and seeded separately. Cells were grown in supplemented DMEM medium, without the addition of any inductive chondrogenic agents. The medium was replaced every 2-3 days for a period of 21 days. Care was taken during media replacement to not disturb the particles in the cultures. The assay was performed in three triplicates.

Following one, two and three weeks in culture, the MSCs differentiation was assayed by staining of the culture with Safranin O/Fast Green staining [Kahveci Z, Minbay F Z, Cavusoglu L (2000) Safranin O staining using a microwave oven. Biotech Histochem. 75(6):264-8] of cells fixed with 4% glutaraldegyde solution. Digital images of the stained cells were processed.

FIG. 7 shows Fast Green staining of cytoplasm of all the cells in a bright green color while Safranin O staining of glycosaminiglycans (GAG) secreted by chondrocytes into the extracellular matrix of the cells is evident by a characteristic pink color.

The images were analyzed using ImageJ software. The color intensity was used to estimate chondrogenesis. Each image was analyzed for the area of stained cells with Safranin O (8A) and its integrated density (8B) of pink color- it was calculated by counting the number of the pink colored pixels in a specified area of the image, excluding the area of the particles from the calculation.

During the entire study aragonite impregnated with hyaluronic acid showed greater chondrogenesis in comparison to aragonite alone both in terms of the stained area (amount of cells) and the color intensity (amount of GAG at the ECM).

Control assay included the assay of cells cultured identically, in the absence of any scaffold, which showed significantly less characteristic toward the GAG staining.

Figure 9A:
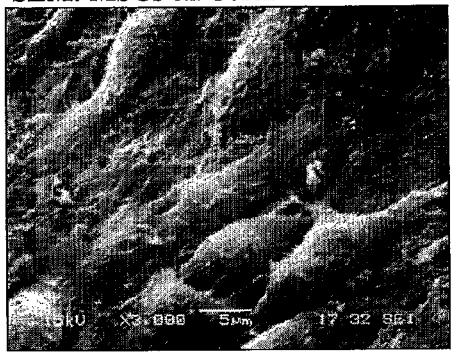
FIGS. 9A and 9B demonstrate the morphology of MSC cultured on coral-based scaffolds versus those cultured on coral and Hyaluronic acid-containing scaffolds (FIGS. 9C and 9D)
Figure 9B:
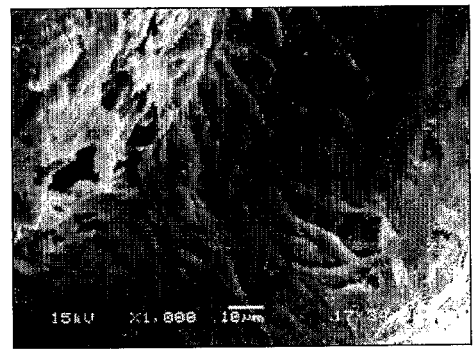
Figure 9C:
FIG. 9 shows SEM micrographs of the MSCs, cultured on the various scaffolds.
Figure 9D:
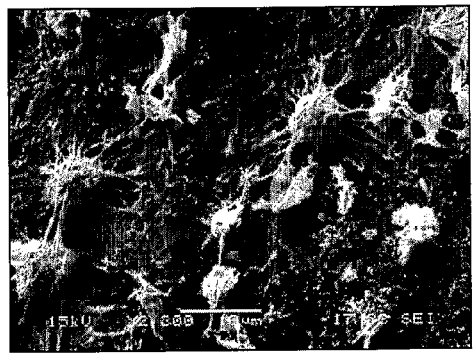

The morphology of the cells was visualized using field emission Scanning Electron Microscopy (JEOL, JSM-7400F). MSCs seeded on the aragonite with hyaluronic acid exhibited a round morphology and developed dense extracellular matrix, which is typical for matured chondrocytes (FIGS. 9C-D). In contrast, the MSCs, grown on aragonite without HA, showed flattened, fibroblast-like morphology (FIGS. 9A-B).

The aragonite-HA complex thus enabled MSC adherence, proliferation and differentiation toward a chondrogenic phenotype.

The chondrogenic potential of the aragonite impregnated with hyaluronic acid was demonstrated herein to provide superior chondrogenesis, thereby supporting the scope of the invention directed to abi-phasic implant where the chondral phase is composed of aragonite with holes/voids that are impregnated with a biocompatible polymer such as hyaluronic acid, and a bone phase which is composed of aragonite or calcite alone.

Example 5

Aragonite and Calcite-Based Scaffolds are Chondrogenic In Vivo

Implantation may be at any suitable location, for example, for knee joint repair, implantation may be within the Medial Femoral Condyle (MFC), Lateral Femoral Condyle (LFC), Patela, Trochlear Groove (TG) and the Tibia.

Model systems using sheep, goats or horses may be utilized to test certain embodied scaffolds of this invention. In the chosen implantation location, for example in the load bearing area of the MFC, a defect is made using a punch. The dimensions of the defect are measured, for example, 5-10 mm and 6-12 mm in diameter and depth respectively.

The diameter of the implant will be appropriate for the diameter of the osteochondral defect being tested. For example, a chosen diameter of an implant may be 6 mm, to covet 5.8 mm diameter of the defect in order to assure good fixation to the defect in a press fit manner. A second location in a non weight bearing place may be chosen, for comparison, for example within the TG. In order to treat large cartilage lesions, several implants, having the same or different geometrical shapes and properties, can be introduced in order to fill the defect. The implantation can be performed arthroscopically or by an open incision (arthrotomy).

X-ray, CT or MRI imaging may be performed to verify the position of the implants.

Example 6

Preparation of a Bi-Phasic Aragonite Scaffold Comprising Holes and Hyaluronic Acid at the Chondral Phase for Packaging and Distribution Preparation of the aragonite core scaffold: Coral from the hydrocoral Porites Lutea which has an average pore size of 100-150 μm is harvested, evaluated visually for its appearance, density, and porosity, and is subjected to FTIR analysis. Amino acid quantification may also be determined. Coral is then immersed in 5% sodium hypochlorite for removal of external organic tissue.

Without being bound by theory, one means by which superior scaffolding is produced by this process is a result of the penetration deep within the coral, whereas immersion processes or application of positive pressure during purification allows for air bubbles to remain trapped within the pore network of the scaffold, resulting in poor accessibility of the solvents to inner compartments of the coral. Moreover, the purification process facilitates removal of the oxidizing agents employed in a most thorough manner, a clearly desirable result for scaffolding later implanted in living beings.

Figure 10A:
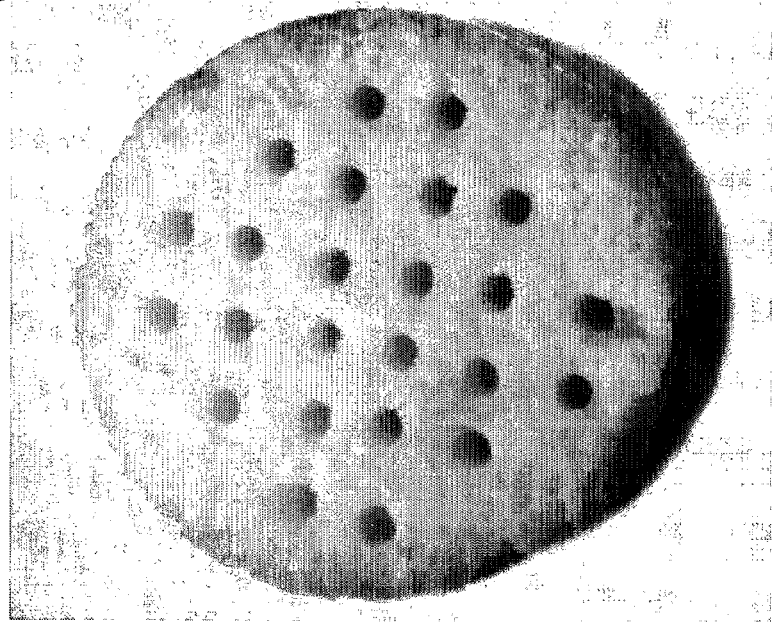
FIG. 10 shows an embodiment of a scaffold of this invention demonstrating a pattern of drilled holes in the chondral phase of an embodied implant, prior to (FIG. 10A) and following (FIG. 10B) impregnation of the scaffold with a NaHA 1% solution followed by evaporation.
Figure 10B:
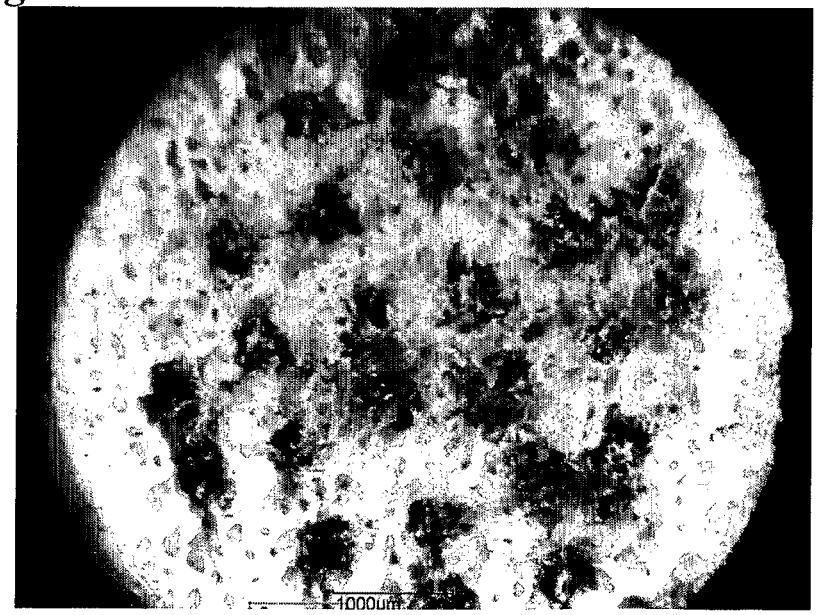

A saw, for example, a diamond disk saw, is used to remove the outer coral layer, and plugs of the desired dimensions are cut from a larger coral block. A series of holes are then drilled through part of the plugs thus obtained, to a desired depth and in a desired pattern/number, etc., see for example, FIGS. 10A and 10B.

Organic matter is removed from the coral as follows: the plugs are first exposed to fluid containing an oxidizing agent under negative pressure, for example, a 5% sodium hypochlorite solution for 30 minutes, 3 exchanges at temperature range RT at 50° C., and subatmospheric pressure using vacuum pressure ranging from 0.2-0.00001 Bar. The plugs are then exposed to a 10% solution of hydrogen peroxide for 15 minutes at a temperature range of from RT-50° C., and subatmospheric pressure using vacuum pressure ranging from 0.2-0.00001 Bar. The cleaned plugs are then washed in distilled water for 30 minutes, 3 exchanges at a temperature range of from RT-50° C., and subatmospheric pressure using vacuum pressure ranging from 0.2-0.00001 Bar.

The coral is sterilized by exposure to gamma radiation at a strength of at least 22.5 kGy and can then be stored aseptically, in packaging material.

Sodium hyalronate 1% (hyaluronic acid 1% solution in phosphate buffered saline, described hereinabove) is applied apically to the plug. An apical portion of the plug is constrained within a ring, for example a silicon ring, which spans a region above the terminus of the plug creating a reservoir at the terminus of the plug. Hyaluronic acid solution is then applied to the reservoir region, for example, 70 ml of the solution is applied over a 6 mm in diameter plug to produce 2 mm homogenous phase of coral with holes impregnating the hyaluronic acid to treat the chondral defect, which is immobilized in a silicon ring which spans the plug terminus and 4 mm above the terminus. The application of the hyaluronic acid solution proceeds for 45-60 minutes, and the ring is then removed. The plug is inserted in a sterile packaging and sealed. The sealed packaging is then subjected to evaporation under vacuum conditions to dry out the plug from the NaHA 1% solution to form dried HA coating of the chondral phase of the plug (e.g. by lyophilization/dessication). A sterile pack containing the dried product is thereby obtained.

FIG. 11 schematically depicts an embodied scaffold of the invention, wherein a first phase 11-10 comprising a series of holes or voids 11-30 is shown atop a second phase 11-20. The terminus of the second phase may be tapered 11-40 to allow for easy tight fitting of the scaffold in question.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A scaffold for tissue repair, said scaffold consisting essentially of two phases wherein:
   a first phase of said two phases comprises solid coral and a biocompatible polymer, wherein said biocompatible polymer comprises a glycosaminoglycan comprising hyaluronic acid, sodium hyaluronate, cross-linked hyaluronic acid or combinations thereof, wherein said first phase further comprises a series of hollows along a longitudinal axis in said first phase, and wherein said biocompatible polymer penetrates to within said hollows; and
   a second phase of said two phases comprises a solid coral.

2. The scaffold of claim 1, where said biocompatible polymer further comprises another glycosaminoglycan, collagen, elastin, silk, chitosan, alginate, or a combination thereof.

3. The scaffold of claim 2, wherein said glycosaminoglycan is hyaluronic acid or sodium hyaluronate.

4. The scaffold of claim 1, wherein said biocompatible polymer further comprises a synthetic biodegradable polymer, which comprises alpha-hydroxy acids.

5. The scaffold of claim 1, wherein said scaffold further comprises a cytokine, a chelator, a cell population, an anti-inflammatory compound, an anti-infective compound, a growth factor, an antibiotic, a pro-angiogenic factor, a therapeutic compound, or any combination thereof.

6. The scaffold of claim 5, wherein said cell population comprises mesenchymal stem cells, osteoblasts, osteocytes, osteoclasts, chondroblasts, chondrocytes, fibroblasts, or a combination thereof, or other cells involved in cartilage or bone repair.

7. The scaffold of claim 5, wherein said growth factor is epidermal growth factor (EGF), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or a combination thereof.

8. The scaffold of claim 1, wherein said scaffold approximates the form of a cylinder, cone, screw, rectangular bar, plate, disc, pyramid, granule, ball or cube.

9. The scaffold of claim 1, wherein the scaffold assumes a shape to approximate a meniscus for a knee or elbow; a joint; an articular surface of a bone, a portion of a rib cage, a hip, a pelvis, an ear, a nose, a ligament, a bronchial tube or an intervertebral disc.

10. The scaffold of claim 1, wherein said scaffold is cylindrical in shape and has a diameter of about 5-40 mm, and a height of about 5-25 mm.

11. The scaffold of claim 1, wherein said biocompatible polymer is in the form of a polymer coating, forming a polymer layer associated with a portion of said scaffold.

12. The scaffold of claim 11, wherein said polymer coating is present at a terminus of said scaffold and said coating has a thickness of between about 0.1-10 mm.

13. The scaffold of claim 4, wherein said alpha-hydroxy acids comprise poly-lactic acid, polyglycolic acid, enantioners thereof, co-polymers thereof, polyorthoesters, or combinations thereof.

14. A method of inducing or enhancing repair, regeneration or enhancement of formation of cartilage, bone or a combination thereof, said method comprising implanting in a subject, a scaffold of claim 1 within a site in need of repair, regeneration or enhancement of formation of cartilage, bone or a combination thereof in said subject.

15. The method of claim 14, wherein said cartilage defect or disorder comprises a full or partial thickness articular cartilage defect; osteochondral defect; osteoarthritis; osteochondritis dissecans; a joint defect; or a defect resulting from trauma, sports, or repetitive stress.

16. The method of claim 14, wherein said scaffold is positioned such that said at least a second porous phase is implanted within or proximally to cartilage tissue and said at least a first porous phase is implanted within or proximally to bone tissue.

17. A kit for repair of cartilage or bone comprising the scaffold of claim 1, and directions for utilizing said scaffold in tissue repair.

18. The kit of claim 17, which further comprises a tool or tools for optimal insertion of said scaffold.

19. The kit of claim 17, which further comprises a series of scaffolds of different sizes or shapes.

20. The kit of claim 17, which further comprises a tool or tools for optimal insertion of said scaffold, and a series of scaffolds of different sizes or shapes.

* * * * *